US006852530B2

(12) United States Patent
Silver et al.

(10) Patent No.: US 6,852,530 B2
(45) Date of Patent: Feb. 8, 2005

(54) SELF-EXTINGUISHING RECOMBINASES, NUCLEIC ACIDS ENCODING THEM AND METHODS OF USING THE SAME

(75) Inventors: Daniel P. Silver, Wayland, MA (US); David M. Livingston, Brookline, MA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 4 days.

(21) Appl. No.: 09/834,778

(22) Filed: Apr. 12, 2001

(65) Prior Publication Data

US 2002/0062489 A1 May 23, 2002

Related U.S. Application Data

(60) Provisional application No. 60/196,338, filed on Apr. 12, 2000.

(51) Int. Cl.[7] .................... C12N 15/85; C12N 15/63; A61K 48/00; A01K 67/00
(52) U.S. Cl. ................ 435/325; 435/320.1; 514/44; 800/8
(58) Field of Search .................. 435/320.1, 325; 514/44; 800/8

(56) References Cited

U.S. PATENT DOCUMENTS

| 4,959,317 A | 9/1990 | Sauer .................... 435/462 |
| 5,629,159 A | 5/1997 | Anderson ................... 435/6 |
| 5,885,836 A | 3/1999 | Wahl et al. ................ 435/455 |
| 6,025,192 A | 2/2000 | Beach et al. ............. 435/322.1 |
| 6,140,129 A | 10/2000 | Cox et al. ................ 435/477 |
| 6,175,058 B1 | 1/2001 | Baszczynski et al. ........ 800/278 |
| 6,200,800 B1 | 3/2001 | Choulika et al. ......... 435/320.1 |

FOREIGN PATENT DOCUMENTS

| DE | 195 30 412 | | 2/1997 |
| WO | WO 97/06271 | * | 2/1997 |

OTHER PUBLICATIONS

Sauer, Multiplex cre/lox recombination permits selective site–specific DNA targeting to both a natural and an engineered site in the yeast genome, 1996, Nucleic Acids Research, vol. 24, pp. 4608–4613.*
Gagneten et al., Brief expression of a GFP cre fusion gene in embryonic stem cells allows rapid retrieval of site–specific genomic deletions, 1997, Nucleic Acids Research, vol. 25, pp. 3326–3331.*
Miyoshi et al., Development of a self–inactivating lntivirus vector, 1998, Journal of Virology, p. 8150–5157.*
Abremski et al. (1983). "Studies on the Properties of P1 Site–Specific Recombination: Evidence for Topologically Unlinked Products Following Recombination" *Cell 32*: 1301–1311.
Abremski and Hoess (1984). "Bacteriophage P1 Site–specific Recombination" *J. Biol. Chem. 259*(3): 1509–1514.

Amin et al. (1990). "Synaptic Intermediates.Promoted by the FLP Recombinase" *J. Mol. Biol. 214*: 55–72.
Buchholz et al. (1998). "Improved properties of FLP recombinase evolved by cycling mutagenesis" *Nat. Biotechnol. 16*(7): 657–662.
Cox (1989). "DNA Inversion in the 2µm Plasmid of *Saccharomyces cerevisiae*" *Mobile DNA*. pp. 661–670. (American Soc. Fo Microbiology, Wash., DC).
Craig (1988). "The Mechanism of Conservative Site–Specific Recombination" *Ann. Rev. Genet. 22*: 77–105.
Cregg and Madden (1989). "Use of site–specific recombination to regenerate selectable markers" *Mol. Gen. Genet. 219*: 320–323.
Echols (1990). "Nucleoprotein Structures Initiating DNA Replication, Transcription, and Site–specific Recombination" *J. Biol. Chem. 265*: 14697–14700.
Falco et al. (1982). "Genetic Properties of Chromosomally Integrated 2µ Plasmid DNA In Yeast" *Cell 29*:573–584.
Flanagan and Fennewald (1989). "Analysis of Inhibitors of the Site–specific Recombination Reaction Mediated b Tn3 Resolvase" *J. Mol. Biol. 206*: 295–304.
Glasgow et al. (1989). "DBA–binding Properties of the Hin Recombinase" *J. Biol. Chem. 264*(17): 10072–10082.
Golic and Lindquist (1989). "The FLP Recombinase of Yeast Catalyzes Site–Specific Recombination in the Drosophila Genome" *Cell 59*:499–509.
Gossen and Bujard (1992). "Tight control of gene expression in mammalian cells by tetracycline–responsive promoters" *Proc. Natl. Acad. Sci USA 89*: 5547–5551.
Hafter and Bickle (1988). "Enhancer–Independent mutants of the Cin recombinase have a relaxed topological specificity" *EMBO J. 7*(12): 3991–3996.
Hamilton and Abremski (1984). "Site–specific Recombination by the Bacteriophage P1 lox–Cre system" *J. Mol. Biol. 178*: 481–486.
Hoess et al. (1982). "P1 site–specific recombination: Nucleotide sequence of the recombining sites" *Proc. Natl. Acad. Sci. USA 79*: 3398–3402.
Hoess et al. (1984). "The Nature of the Interaction of the P1 Recombinase Cre with the Recombining Site loxP" *Cold Spring Harbor Symp. Quant. Biol. 49*: 761–768.
Hoess et al. (1986). "The role of the loxP spacer region in P1 site–specific recombination" *Nucleic Acids Res. 14*(5): 2287–2300.

(List continued on next page.)

*Primary Examiner*—David Guzo
*Assistant Examiner*—Daniel M. Sullivan
(74) *Attorney, Agent, or Firm*—Mintz, Levin, Cohn, Ferris Glovsky and Popeo, P.C.; Ivor R. Elrifi; Christina K. Stock

(57) ABSTRACT

Nucleic acid molecules comprising at least a first signal site and a recombinase gene operably linked to an expression control sequence, such that upon entry into a cell, there is a first signal site and a second signal site positioned to mediate excision of a sufficient portion of either the recombinase gene or the expression control sequence to extinguish recombinase activity when the first and second signal sites are contacted with a recombinase, cells, transgenics and uses of the foregoing.

20 Claims, 9 Drawing Sheets

OTHER PUBLICATIONS

Hubner et al. (1989). "Bent DNA is Needed for Recombinational Enhancer Activity in the Site–Specific Recombination System Cin of Bacteriophage P1" *J. Mol. Biol. 205*: 493–500.

Hunger–Bertling et al. (1990). "Short DNA fragments induce site–specific recombination in mammalian cells" *Mol. Cell. Biochem. 92*: 107–116.

Kellendonk et al. (1996). "Regulation of Cre recombinase activity by the synthetic steroid RU 486" *Nucleic Acids Res. 24*(8): 1404–1411.

Kilby et al. (1993). "Site–specific recombinases: tools for genome engineering" *Trends Genet. 9*: 413–421.

Kuhn et al. (1995). "Inducible Gene Targeting in Mice" *Science 269*: 1427–1429.

Lee and Saito (1998). "Role of nucleotide sequences of loxP spacer region in Cre–mediated recombination" *Gene 216*: 55–65.

Lewandowski and Martin (1997). "Cre–mediated chromosome loss in mice" *Nat. Genet. 17*: 223–225.

Mercier et al. (1990). "Structural and Functional Characterization of tnpl, a Recombinase Locus in Tn21 and Related β–Lactamase Transposons" *J. Bacteriol. 172*(7): 3745–3757.

Malynn et al. (1988). "The*scid* Defect Affects the Final Step of the Immunoglobulin VDJ Recombinase Mechanism" *Cell 54*: 453–460.

Matsuzaki et al. (1990). "Chromosome Engineering in *Saccharomyces cerevisiae* by Using a Site–specific Recombination System of a Yeast Plasmid" *J. Bacteriol 172*(2): 610–618.

Metzger et al. (1995). "Conditional site–specific recombination in mammalian cells using a ligand–dependent chimeric Cre recombinase" *Proc. Natl. Acad. Sci. USA 92*: 6991–6995.

Muller (1999). "Ten years of gene targeting: targeted mouse mutants, from vector design to phenotype analysis" *Mech. Dev. 82*: 3–21.

Nagy (2000). "Cre Recombinase: The Universal Reagent for Genome Tailoring" *Genesis 26*: 99–109.

Parsons et al. (1990). "Functional Analysis of Arg–308 Mutants of Flp Recombinase" *J. Biol. Chem. 265*(8): 4527–4533.

Poyart–Salmeron et al. (1989). "Molecular characterization of two proteins involved in the excision of the conjugative transposon Tn1545: homologies with other site–specific recombinases" *EMBO J. 8*(8): 2425–2433.

Rajewsky et al. (1996). "Perspective Series: Molecular Medicine in Genetically Engineered Animals" *J. Clin. Invest. 98*(3): 600–603.

Ramirez–Solis et al. (1995). "Chromosome engineering in mice" *Nature 378*: 720–724.

Rossant and McMahon (1999). "Cre'–ating mouse mutants—a meeting review on conditional mouse genetics" *Genes Dev. 13*: 142–145.

Sato et al. (1990). "The cisA Cistron of *Bacillus subtilis* Sporulation Gene spoIVC Encodes a Protein Homologous to a Site–Specific Recombinase" *J. Bacteriol. 172*(2): 1092–1098.

Sauer (1992). "Identification of Cryptic Iox Sites in the Yeast Genome by Selection for Cre–mediated Chromosome Translocations that Confer Multiple Drug Resistance" *J. Mol. Biol. 223*: 911–928.

Sauer (1998). "Inducible Gene Targeting in Mice Using the Cre/lox System" *Methods 14*: 381–392.

Sauer and Henderson (1988). "Site–specific DNA recombination in mammalian cells by the Cre recombinase of bacteriophage P1" *Proc. Natl. Acad. Sci. USA 85*: 5166–5170.

Schlake and Bode (1994). "Use of Mutated FLP Recognition Target Sites for the Exchange of Expression Cassettes at Defined Chromosomal Loci" *Biochem. 33*: 12746–12751.

Schmidt et al. (2000). "Illegitimate Cre–dependent chromosome rearrangements in transgenic mouse spermatids" *Proc. Natl. Acad. Sci. USA 97*(25): 13702–13707.

Schwartz and Sadowski (1989), "FLP Recombinase of the 2 μm Circle Plasmid of the *Saccharomyces cerevisiae* Bends Its DNA Target" *J. Mol. Biol. 205*: 647–658.

Stark et al. (1989). "Site–Specific Recombination by Tn3 Resolvase: Topological Changes in the Forward and Reverse Directions" *Cell 58*: 779–790.

Sternberg and Hamilton (1981). "Bacteriophage P1 Site–specific Recombination" *J. Mol. Biol. 150*: 467–486.

Sternberg et al. (1986). "Bacteriophage P1 cre Gene and its Regulatory Region" *J. Mol. Biol. 187*: 197–212.

St. Onge et al. (1996). "Temporal control of the Cre recombinase in transgenic mice by a tetracycline responsive promoter" *Nucleic Acids Res. 24*(19): 3875–3877.

Thyagarajan et al. (2000). "Mammalian genomes contain active recombinase recognition sites" *Gene 244*: 47–54.

de Villartay et al. (1988). "Deletion of the human T–cell receptor δ–gene by a site–specific recombination" *Nature 335*: 170–174.

Weisberg and Landy (1983). "Site–specific Recombination in Phage Lambda" *Lambda II*. pp. 211–250. (Cold Springs Harbor Press).

Zhang et al. (1996). "Inducible site–directed recombination in mouse embryonic stem cells" *Nucleic Acids Res. 24*(4): 542–548.

Russ et al. (1996). "Self–Deleting Retrovirus Vectors for Gene Therapy" *J. Virol. 70*(8): 4927–4932.

Bunting et al. (1999). "Targeting genes for self–excision in the germ line" *Genes& Development 13*(12): 1524–1528.

Choulika et al. (1996). "Transfer of Single Gene–Containing Long Terminal Repeats into the Genome of Mammalian Cells by a Retroviral vector Carrying the cre Gene and the IoxP Site" *J. Virol. 70*(3): 1792–1798.

Silver et al. (2001). "Self–Excising Retroviral Vectors Encoding the Cre Recombinase Overcome Cre–Mediated Cellular Toxicity" *Mol. Cell 8*(1): 233–243.

International Search Report for PCT/US 01/12193. Mailed on Nov. 28, 2001.

* cited by examiner

SELF-EXTINGUISHING RECOMBINASES, NUCLEIC ACIDS ENCODING THEM AND METHODS OF USING THE SAME

RELATED APPLICATIONS

This application claims the benefit of U.S. Provisional Application Ser. No. 60/196,338, filed Apr. 12, 2000.

STATEMENT AS TO FEDERALLY SPONSORED RESEARCH

This invention was made with U.S. government support under NIH grant, number CA82572. The government has certain rights in the invention.

FIELD OF THE INVENTION

The invention relates to generally to methods and compositions for the manipulation of DNA sequences, and in particular to methods and compositions for the same, using self-extinguishing recombinases.

BACKGROUND OF THE INVENTION

Cre and other recombinase enzymes of the λ integrase family have opened new possibilities for the genetic manipulation of mammalian genomes (Kilby et al., 1993). These recombinases each cleave DNA at a specific target sequence and ligate the newly exposed ends to the cleaved DNA at a second target sequence. One member of this family, cre recombinase, the 38 kDa product of the bacteriophage P1 cre gene, catalyzes recombination between target sequences termed lox sites (Sternberg and Hamilton, 1981). The lox site is a 34 base pair target sequence consisting of two 13 base pair inverted repeats flanking an 8 base pair core (Hoess et al., 1982). When two lox sites are placed in cis, deletion or inversion of the DNA sequence between the lox sites ensues upon expression of cre, depending on the orientation of the lox sites with respect to each other. When lox sites are arrayed on two separate linear DNA molecules, strand exchange can occur; when present on a circle and a linear molecule, integration of the circle into the linear DNA can result from the action of. The ability to catalyze these reactions efficiently in mammalian cells (Sauer and Henderson, 1988) has enabled complex genetic manipulations of a sort only previously attainable in yeast and prokaryotes.

Of the λ integrase family members, the cre recombinase has become the most commonly employed site-specific recombinase for genetic manipulation, and conditional gene targeting in the mouse is its most frequent use (See Nagy, 2000; Muller, 1999; Rossant and McMahon, 1999; Sauer, 1998; Rajewsky et al., 1996; Kilby et al., 1993). Generally, a segment of a gene to be inactivated or modified by cre-mediated recombination is flanked by lox sites ("floxed allele"); this modification of an endogenous allele is accomplished by homologous recombination in ES cells. Being short sequences, strategically placed lox sites generally do not perturb expression of a target gene. A mouse generated from ES cells harboring a floxed allele can be bred to a mouse transgenic for the cre recombinase. Depending on how the transgenic cre gene is controlled, deletion of a floxed allele can take place in a tissue and/or in a developmentally precise manner, often bypassing lethality at earlier developmental stages or avoiding other unwanted effects.

Ideally, upon synthesis of cre, these cells should facilitate an analysis of the consequences of deleting a floxed allele(s) with precision. However, cre can be overtly toxic to cells, a property that inherently limits its utility. This toxicity depends upon the strand cleavage activity of cre, and is, therefore, intrinsic to its activity as a recombinase. A central feature of the toxicity is genomic instability. Other reasons for limiting the duration and intensity of recombinase expression exist as well, for example the potential antigenicity of a recombinase in a foreign host.

Thus, a need remains in the art for the creation of a recombinase system that eliminates recombinase-mediated toxicity or other undesired effects, but yet retains the ability to effect site-specific recombination.

SUMMARY OF THE INVENTION

The invention described herein includes the use of a self-extinguishing recombinase (e.g., cre or Flp) to effect any change on any other sequence, or a sequence including a region encoding the recombinase itself, in any context, e.g., in a plant, an animal, a cell, or in vitro. In one aspect, the invention relates to a system based upon self-excision by a selected recombinase of its own coding sequence that limits the duration and intensity of the recombinase expression so that the recombinase expression is sufficient for deletion of a sequence flanked on each side by a signal site, and then further recombinase expression is then terminated. The invention provides nucleic acid molecules comprising at least a first signal site and a recombinase gene operably linked to an expression control sequence, such that upon entry into a cell, there is a first signal site and a second signal site positioned to mediate excision of a sufficient portion of either the recombinase gene or the expression control sequence to extinguish recombinase activity when the first and second signal sites are contacted with a recombinase and recombination occurs. Vectors of the invention are useful as research reagents, as well in the in vivo controlled delivery of diagnostic and therapeutic agents. Vectors of the invention are also useful in the production of agriculturally important transgenic plants, transgenic animals useful in research, and transgenic proteins. For example, the vectors of the invention can be used in the production of therapeutic proteins, such as tPA, in the milk of transgenic mammals. Accordingly, cells and transgenic plants and animals containing such nucleic acid molecules are also provided. Additionally, such cells and transgenic plants and animals may also contain a target gene and signal sequences recognized by the recombinase. Multiple recombinases may be used. Other features and advantages of the invention will be apparent from the following detailed description and claims.

DETAILED DESCRIPTION OF THE INVENTION

Figure 1:
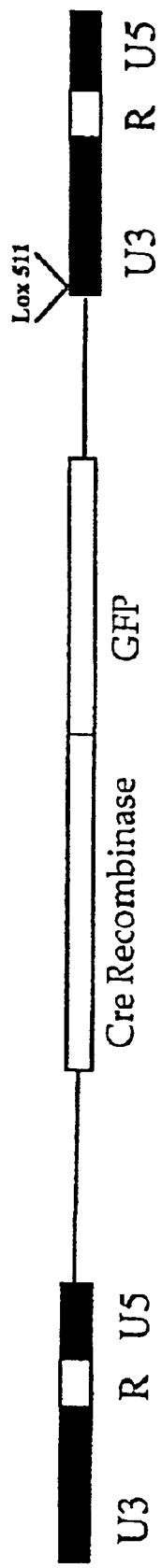
FIG. 1 is a schematic representation of a viral vector of the invention, in which a Cre-encoding gene and a lox site are present.

The invention is based in part on the discovery that continuous expression of the cre recombinase in tissue culture cells lacking exogenous target lox sites causes decreased growth, cytopathic effects, and chromosomal aberrations. cre mutants that bind to lox sites but do not cleave DNA do not show these toxic effects. Thus, a self-excising retroviral vector encoding cre that incorporates a negative feedback loop to limit the duration and intensity of cre expression has been found to avoid measurable toxicity, to retain the ability to excise a floxed target sequence, and to provide the basis of a general strategy for genome engineering with cre or similar recombinases. The present invention is based upon the design of a self-excising cre-lox system, wherein cre excises its own coding sequence, thus limiting the duration and intensity of cre expression. Continued toxicity, immunogenicity, allergy or other unwanted effects potentially caused by continued recombinant expression are avoided.

In a first aspect, the present invention is directed to a system based upon self-excision by a selected recombinase of its own coding sequence that limits the duration and intensity of the recombinase so that the recombinase expression is sufficient for deletion of a sequence flanked on each side by a recognition site.

In a preferred embodiment, the selected recombinase is cre, and the corresponding recognition sequences are lox sites. Many other recombinases, such as Flp, and their cognate signal sequences are known in the art, and can be used in any of the nucleic acid molecules and methods described herein.

In a second aspect, the present invention is directed to a general method that minimizes recombinase toxicity to cells or any other undesirable property associated with the recombinase to cells or the host organism. These undesirable properties include, but are not limited to, genomic or chromosomal instability, growth arrest or retarded growth, cytopathic effect, and antigenicity. In this method, signal sequences recognized by a recombinase are positioned with respect to the recombinase gene or a regulatory element (e.g., a promoter, enhancer, or other transcriptional activator sequence) of the recombinase gene so that recombination results in inactivation or diminution of expression of the recombinase. Thus, signal sequences can be positioned so as to flank a recombinase gene or a regulatory element of a recombinase gene.

In a preferred embodiment, the DNA encoding the recombinase (i.e. cre recombinase) is itself flanked by the signal sequences or signal sites recognized by the recombinase (i.e. lox sites.) Both the terms signal sequence and signal site can be used interchangably to mean the sequence that the recombinase recognizes; nucleic acid sequences between two signal sites are deleted or inverted if the signal sites are on the same nucleic acid molecule, and sequences are joined if the two signal sites are on different nucleic acid molecules. Thus, when the recombinase has been produced in sufficient quantity to have effected a desired recombination with respect to a given target gene or sequence, the recombinase, acting on the signal sites flanking the recombinase coding sequences, excises the recombinase gene, thus creating a negative feedback loop that limits the continued production of the recombinase itself and stops production of the target protein or otherwise modifies the target.

In a third aspect, the present invention is directed to a nucleic acid molecule that includes a sequence encoding a recombinase and a signal sequence recognized by the recombinase. For example, the nucleic acid molecule can be included in a retroviral vector, and the signal sequence can be inserted into a retroviral long terminal repeat (e.g., into the U3 region of the 3' long terminal repeat) of such a vector.) See, e.g., FIG. 1.

In a preferred embodiment, the nucleic acid molecule can also include two signal sequences that are recognized by the recombinase and are positioned with respect to the sequence encoding the recombinase so that recombination by the recombinase inactivates or decreases expression of the recombinase by deletion or disablement. For example, the signal sequences can flank the sequence encoding the recombinase or a positive regulatory element (e.g., a promoter, enhancer, or other transcriptional activator sequence (e.g., a transcription factor binding site)) of the sequence encoding the recombinase, or can flank another sequence important for recombinase expression, such as a sequence encoding, or involved in regulation of expression of, a transcription factor.

The sequences are said to "flank" the gene encoding the recombinase (or regulatory element, e.g., expression control sequence) if they are located on either side of that gene or regulatory sequence.

In another embodiment of the present invention, the nucleic acid molecules of the invention can be used as research reagents or they can be used in other contexts, including the control of expression of therapeutic, diagnostic, or other agents in cells, plants, and animals. Accordingly, the invention provides a cell including any of the nucleic acid molecules containing a sequence encoding a recombinase described herein. In addition, the cell can contain a second nucleic acid molecule, covalently linked or unlinked, overlapping or not, including a target gene and signal sequence or signal sequences recognized by the recombinase. In such a cell, the recombinase, when expressed, can excise, invert or otherwise modify a sequence in the second nucleic acid molecule that is located adjacent to or between the signal sequences in the second nucleic acid molecule. This excision, inversion, or other modification can result in modulation of expression of the target gene.

In one example, two signal sequences in the second nucleic acid molecule are in the same, or direct, orientation with respect to one another. Such signal sequences can, for example, flank the target gene, so that expression of the recombinase results in excision of the target gene and inactivation of expression of the target gene; flank a positive regulatory element of the target gene, so that expression of the recombinase results in excision of the positive regulatory element and inactivation of expression of the target gene; or flank a negative regulatory element of the target gene (endogenous or previously introduced), so that expression of the recombinase results in excision of the negative regulatory element and activation of expression of the target gene.

Alternatively, the signal sequences in the second nucleic acid molecule can be in a different, or an inverted, orientation with respect to one another. Such signal sequences can, for example, flank an inverted positive regulatory element of the target gene or an inverted coding region of the target gene, so that expression of the recombinase results in inversion of the inverted positive regulatory element or inversion of the inverted coding region, and activation of expression of the target gene. As another example, the signal sequences can flank an inverted negative regulatory element of the target gene or a coding region of the target gene, so that expression of the recombinase results in inversion of the inverted negative regulatory element or inversion of the coding region, and inactivation of expression of the target gene.

The first and second nucleic acid molecules described above can be part of the same vector or they can be carried on separate vectors. If the first and second nucleic acid molecules are part of the same vector, they can both be expressed from the same promoter, at the same time. Alternatively, the two sequences can be part of the same or different vectors and be controlled by different inducible promoters, which can be turned on independently, at different times. Furthermore, the signal sites that the recombinase recognizes to extinguish its own expression may be the very same signal sites used to modify the target or may be different signal sites. In any case, promoters and other variables used in the invention can be selected to ensure that a certain, predetermined level of expression of a target gene occurs, or that a certain, predetermined length of time passes, prior to inactivation.

The present invention also includes transgenic, non-human animals that contain any of the cells described herein. For example, the invention includes an animal in which the target gene is in such a cell encodes a protein to be made in a targeted secretion of the animal (see below). Also included in the invention are transgenic plants including any of the cells described herein. As a specific example, such a plant may contain a first tissue (e.g., an edible tissue) and a second tissue (e.g., an inedible tissue), and the sequence encoding the recombinase may be expressed in the first tissue, but not in the second tissue. Thus, expression of an exogenous product, such as a disease resistance protein, in the plant can be specifically inactivated in the edible portion of the plant by excision with the recombinase. These and other methods are described further below.

The invention also provides a method for modulating the expression of a target gene in a cell, by introducing into the cell a first nucleic acid molecule including a region encoding a recombinase and signal sequences recognized by the recombinase, and a second nucleic acid molecule including a target gene and signal sequences recognized by the recombinase. The recombinase, when expressed in the cell, excises or inverts a sequence in the second nucleic acid molecule that is flanked by the signal sequences in the second nucleic acid molecule, and the excision or inversion results in modulation of expression of the target gene. Also, the recombinase excises or inverts a sequence in the first nucleic acid molecule that is flanked by the signal sequences in the first nucleic acid molecule, and the excision or inversion inactivates expression of the recombinase. The cell in this method can be, for example, any of those described herein (e.g., those described above). Thus, the recombination can result in the excision or inversion of a sequence, and/or the activation or inactivation of a gene, as is described above. Also, the cell can be present in an animal, such as a mammal (e.g., a human, mouse, goat, pig, or cow), and the target gene in such an animal can encode a diagnostic, therapeutic, or other agent, as is described her below. The cell can also be present in a plant, and, as is discussed further below, it may be desirable to induce expression of the recombinase in such a plant just prior to harvest, for example, between one day and one week prior to harvest.

In another aspect, the nucleic acid molecules, cells, and methods of the present invention also include deleting genes or regulatory elements that are involved in the expression or activity of such an agent. This may be desirable, for example, if more than one element act together to effect expression of an agent, as deletion of one of the elements can be used to decrease, rather than eliminate, expression of the agent. As is described further below, in addition to deletion of a negative regulatory element or inversion of an inverted positive regulatory element, activation of a gene can be achieved according to the invention by removing a sequence inserted into the gene or a regulatory element of the gene by artifice. For example, as is described below, a polyadenylation signal or other sequence that is flanked by lox sites can be inserted, for example, between the promoter of a gene and coding sequences. Removal of the polyadenylation signal or other sequence by expression of the recombinase can then be carried out to allow the cell to initiate expression of the coding sequences. Thus, the invention provides a mechanism for avoiding potential complications of ongoing recombinase expression. The invention also includes, as is described below, the use of multiple recombinases and different target genes, together or sequentially, to regulate gene expression.

The present invention is based on the discovery that prolonged or chronic expression of cre recombinase revealed that chronic cre expression is 'toxic' to a variety of tissue culture cells. Toxicity required the strand-cutting ability of the recombinase; mutant cre recombinases that retain binding to target lox sites but fail to cleave were not toxic. In addition, toxicity was associated with aneuploidy and a high incidence of chromosomal aberration. One possible explanation for these observations is that mammalian genomes contain a number of endogenous sequences that can function as targets for cre (pseudo-lox sites), and continuous exposure to the enzyme is sufficient for cleavage of and, possibly, recombination among them.

In the absence of mechanisms that can effectively deal with the damage associated with ongoing enzyme activity, significant genetic instability might ensue. There is considerable evidence in the literature that supports such a model. For example, cre is capable of recognizing and catalyzing recombination at a diversity of sites related to a canonical lox site. Sauer has found at least ten such sites in the yeast genome (Sauer, 1992), and demonstrated cre-dependent mitotic crossovers at one of these endogenous sites (Sauer, 1996). Moreover, by searching sequence databases, Thyagarajan et al. have detected lox-related sites in the mouse and human genome. The cre recombinase can cleave these sites when they are present on plasmids (Thyagarajan et al., 2000). Therefore, endogenous lox-like sequences that might serve as substrates for the cre recombinase exist in the mammalian genome.

Figure 8:
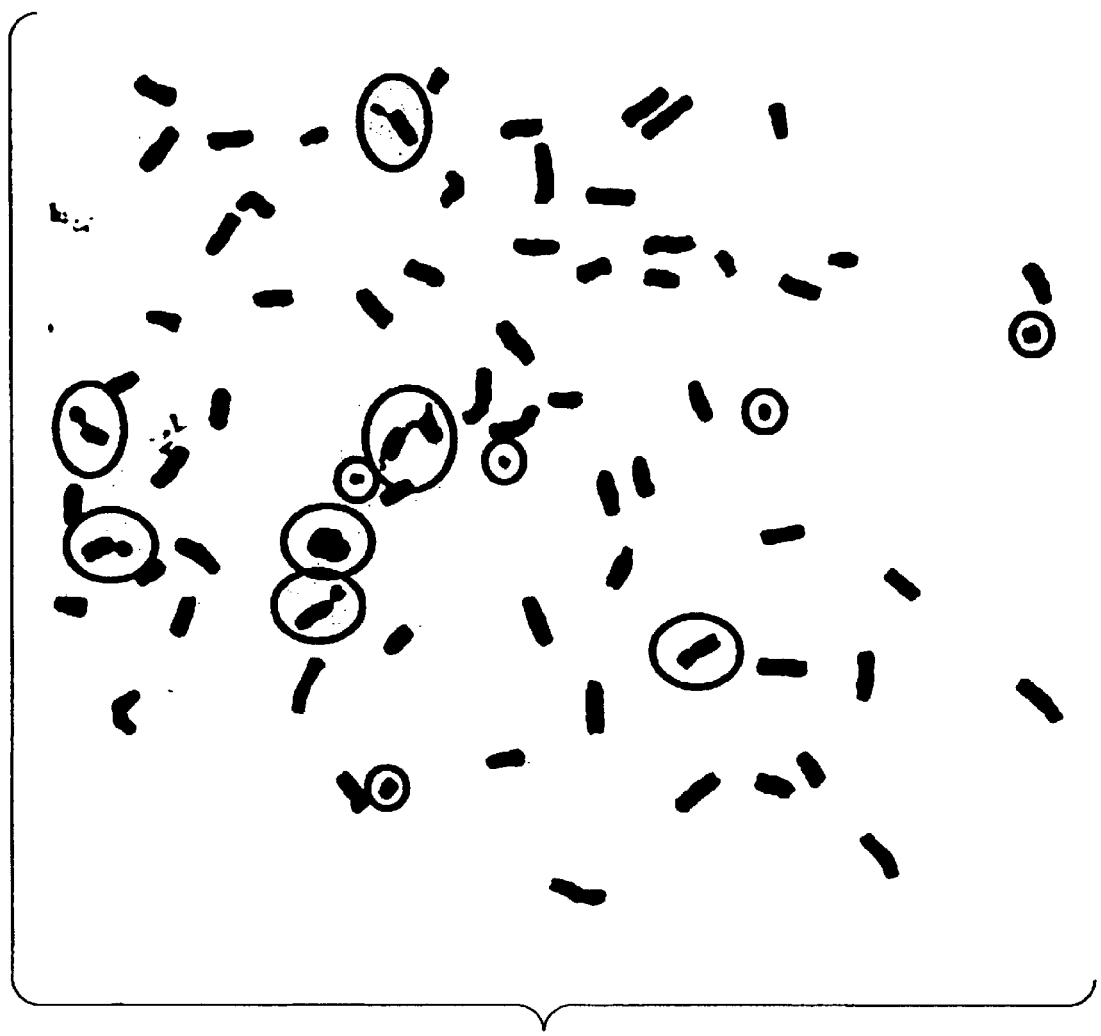
FIG. 8 depicts multiple chromosomal aberrations that were detected in wt MEFs infected with MMPcreGFP.

As an example of the damage that might emerge when cre recombination occurs at selected genomic sites, recombination between ectopically introduced lox P sites on the same chromosome in the mouse can produce deletions, duplications, and dicentric or acentric chromosomes. These outcomes depend upon the orientation of the lox P sites with respect to one another and whether or not the lox P sites involved in a given recombination event are syntenic or are located on sister chromatids or homologues (Falco et al., 1982; Lewandoski and Martin, 1997; Ramirez-Solis et al., 1995). In addition, interchromosomal recombination events between pseudo-lox sites could lead to a variety of lesions. In keeping with this model, stable cre synthesis in otherwise unmanipulated MEFs led to aneuploidy and abnormalities in chromosome structure (FIG. 8 and Table 1). In light of the existence of endogenous lox-like sequences in mammals and of discrete chromosomal abnormalities arising from cleavage at defined chromosomal lox sites, chromosomal abberations in unmodified mouse embryo fibroblasts harboring no exogenous lox sites are not surprising.

Table 1. Wt MEFs Infected with MMPCreGFP Have an Increase in Chromosomal Aberrations. Multiple metaphase spreads from mock-infected cells and cells infected with MMPCreGFP, a virus encoding a Cre-GFP fusion, MMPCreGFPR173K, an identical virus to MMPCreGFP except encoding a Cre mutant allele that binds lox sites but is unable to recombine them, and HR-MMPCreGFP, a virus identical to MMPCreGFP except encoding a lox site in the 3' LTR so as to be self-extinguishing, were prepared as in FIG. 8 and scored for chromosomal abnormalities. 'Total number of abnormal chromosomes' refers to the number of such chromosomes in 48 metaphase spreads. The murine diploid chromosome number is 40.

some seemingly healthy cre transgenic animals manifest subtle cre-dependent toxic phenotypes when studied closely. Data presented here lead to the prediction that establishing transgenic animal lines that uniformly and constitutively express high levels of cre in certain tissues might not be attainable. Of special importance, the potential for mutagenesis by the cre recombinase should be taken into account in proposals calling for its use in gene therapy protocols. In addition, the results presented here point to another hidden danger associated with cre use in eukaryotic cells. If there is a cellular or organ-related phenotype associated with cre excision of a chosen target sequence, one cannot, a priori, be confident that an element of the outcome is not a result of cre attack on endogenous chromosomal lox-like sequences or other non-specific effects. Comparative analysis of cre-treated cells or animals that do and do not carry experimentally introduced lox sites should be considered in this setting.

In the method described herein, the level and duration of cre expression is limited by self-excision to that sufficient for excision of a simple target flanked by lox sites. As shown in the Examples below, this level of expression may not be high in comparison with unrestrained expression from a retroviral LTR (see FIG. 7C). Limiting expression of a given recombinase gene by such a negative feedback approach may provide a general scheme for reducing unwanted toxic effects while preserving the ability to recombine sequences at target signals elsewhere in the genome.

For example, one could produce transgenic mice, either by conventional technology or by homologous recombination in ES cells, in which the cre gene is flanked by lox sites

|  | Total # of Metaphases | Metaphases with Chromosomal Abnormalities (%) | Total Number of Abnormal Chromosomes | Metaphases with N > 41 (%) |
| --- | --- | --- | --- | --- |
| MMPCreGFP | 48 | 21 (44%) | 50 | 18 (38%) |
| MMPCreGFPR173K | 48 | 11 (23%) | 12 | 5 (10%) |
| HR MMPCreGFP | 48 | 7 (15%) | 8 | 2 (4%) |
| Mock | 48 | 11 (23%) | 13 | 8 (17%) |

Recombination between endogenous lox-like sites could produce a variety of genetic lesions. The phenotype of cells bearing these lesions may depend upon cell type and other factors. One manifestation of this effect is the cellular toxicity phenotype observed in cre-expressing human and mouse cells in culture. In this regard, a report has recently appeared describing cre-dependent chromosomal rearrangements leading to sterility in mice targeted to express the cre recombinase in post-meiotic spermatids (Schmidt et al., 2000). As indicated by the Examples below, cre-mediated toxicity can occur in a diversity of cell types and is of general biological relevance and concern.

In addition to the length of time of expression, the intracellular concentration of cre may be an important variable in determining the degree of cellular toxicity and the time when it is first detected. Whether undesirable effects occur incrementally as expression is increased or whether there is a threshold effect is unknown. It may be the case, for example, that selection for low level expression occurs during the generation of certain cre transgenic animals, thereby avoiding lethality. Alternatively, it is possible that and transcribed under the control of a tissue-specific promoter. Conceivably, this approach would permit the construction of a wider library of cre transgenic mice than is currently available. Cells in the tissue where the tissue-specific promoter is active should only produce cre briefly and at low levels. These cells can be identified by the elimination of the cre gene and of any other floxed target that is present in their genome. Tissue specificity and the efficiency of excision can be assessed in this manner. A transgenic mouse carrying a self-excising cre allele under the control of a tissue specific promoter cannot express the cre gene in the germline if the transgene can be successfully transmitted to offspring. This feature may prove beneficial, because any such animals transmitting the transgene across generations must not express cre at appreciable levels in the germline. Therefore, the germline should remain free of cre-mediated toxicity and of any genome aberrations arising from cre activity that might otherwise be inherited. A potential limitation of this method is leaky expression of a recombinase in *E. coli* during cloning manipulations, which could in theory lead to the self-excision of the recombinase in *E. coli*. This problem is easily circumvented; the addition of an intron into the coding sequence of the recombinase or other eukaryotic-specific elements can effectively prevent this problem.

The negative feedback approach has the advantage of limiting cre expression to the level necessary and sufficient for excision; other conditional expression strategies such as those employing the Tet-inducible system (Gossen and Bujard, 1992; St-Onge et al., 1996), steroid receptor gene fusions (Kellendonk et al., 1996; Metzger et al., 1995; Zhang et al., 1996), or interferon regulation (Kuhn et al., 1995) do not have this self-limiting feature. A negative feedback loop could also be combined with these techniques to avoid unnecessary cre expression but still permit regulated induction.

Lastly, the results obtained using the Hit and Run recombinant retrovirus for cre-mediated recombination at lox sites flanking relatively short DNA segments may not be uniformly applicable to other settings where a negative feedback loop might be useful. See e.g., Examples. More complicated situations, such as deletion of megabase stretches of DNA or interchromosomal recombination catalyzed by cre may require modification of the nature of the feedback loop to allow for higher cre expression. For example, if the cre recombinase coding sequence itself is located within a megabase stretch of DNA that is targeted for deletion, a negative feedback loop titrating cre expression to the level required for this type of excision might be achieved and is well within the purview of the method.

Accordingly, the present invention includes the use of a self-inactivating recombinase (e.g., cre or Flp) to effect any change on any other sequence, or a sequence including a region encoding the recombinase itself, in any context, e.g., in a plant, an animal, a cell, or in vitro.

Cre and Flp Recombinase and Lox P and FRT Signal Sites

Cre is a 35 kDa recombinase that can be obtained commercially from, for example, New England Nuclear/Du Pont. The cre gene, which encodes the recombinase, has been cloned and expressed (Abremski et al., Cell 32:1301–1311, 1983). Cre is particularly useful in the invention, because its site-specific recombinase activity is dependent only upon the presence of the lox sites and cre. No energy is needed for this reaction; thus, there is no requirement for ATP or other similar high energy molecules. Moreover, no factors or proteins other than the cre protein is required to mediate sites specific recombination at lox sites (Abremski et al., J. Mol. Biol. Chem. 259:1509–1514, 1984; Hoess et al., Cold Spring Harbor Symp. Quant. Biol. 49:761–768, 1984). In the case of other recombinases, that require other proteins for their expression or activity, it is possible to inactivate the recombinase by deletion of a gene encoding such a protein (or a regulatory element of such a gene), rather than deleting the recombinase gene (or a regulatory element thereof) itself. U.S. Pat. Nos. 4,959,317 and 5,629,159 relating to Cre-lox and use for immortalizing/disimmortalizing cells, are each fully incorporated herein by reference.

Flp is a 48kDa recombinase deriving from the 2 micron circle of the yeast *Saccharomyces cerevisiae* (Cox, M. M. 1989, DNA inversion in the 2 micron plasmid of *Saccharomyces cerevisiae*. In Mobile DNA (Berg, D. E. and Howe, M. M., eds, p 661–670, American Society for Microbiology, Wash, D.C.). Like the cre recombinase, it carries out site-specific recombination, and utilizes a target sequence termed Frt, deleting sequences placed between two Frt elements. Flp is relatively inefficient at 37 degrees Celsius; new alleles of Flp ("enhanced Flp" or "Flpe") have been developed with improved thermal properties through cycling mutagenesis (Buchholz et al., Nat. Biotechnol. 16:7 657–62) (1998). There are also numerous other methods to improve this property that are well known within the art and are implicitly referred to the reference cited above. U.S. Pat. Nos. 5,885,836; 6,140,129; and 6,175,058 relating to FLP/FRT and uses therefor, are each fully incorporated herein by reference.

The lox P site consists of a double-stranded 34 basepair sequence. (SEQ ID NOs:1 and 2, below, each refer to a single strand of this double-stranded sequence.) This sequence contains two 13 basepair inverted repeat sequences that are separated from one another by an 8 basepair spacer region (Hoess et al., Proc. Natl. Acad. Sci. U.S.A. 79:3398–3402, 1982; Sauer, U.S. Pat. No. 4,959,317).

```
                                        (SEQ ID NO:1)
5'-ATAACTTCGTATAATGTATGCTATACGAAGTTAT-3'

(SEQ ID NO:2)
5'-ATAACTTCGTATAGCATACATTATACGAAGTTAT-3'
```

Other lox sites, such as Lox 511 sites (see below) can also be used in the invention, as well as lox sites containing nucleotide substitutions that do not adversely affect recognition by cre (see, e.g., Sauer, Methods: A Companion to Methods in Enzymology 14:381–392, 1998). The minimum Frt site is two inverted 13bp repeats separated by an 8 bp asymmetric spacer; many functional variants of this site exists (see, for example Schlake, T and Bode, J, Biochemistry 1994, 33, 12746–12751).

Although the cre-lox P site-specific recombination system of bacteriophage P1 is preferred (see, e.g., Hamilton et al., J. Mol. Biol. 178:481–486, 1984; Sternberg et al., J. Molec. Biol. 187:197–212, 1986), alternative site-specific recombination systems have been identified, and can be used in accordance with the present invention. For example, the flp recombinase (Schwartz et al., J. Molec. Biol. 205:647–658, 1989; Parsons et al., J. Biol. Chem. 265:4527–4533, 1990; Golic et al., Cell 59:499–509, 1989; Amin et al., J. Molec. Biol. 214:55–72, 1990); the site-specific recombination system of the *E. coli* bacteriophage (Weisberg et al., In: Lambda II, (Hendrix et al., Eds.), Cold Spring Harbor Press, Cold Spring Harbor, N.Y., pp. 211–250 (1983), TpnI and the beta-lactamase transposons (Levesque, J. Bacteriol. 172:3745–3757, 1990); the Tn3 resolvase (Flanagan et al., J. Molec. Biol. 206:295–304, 1989; Stark et al., Cell 58:779–790, 1989); the yeast recombinases (Matsuzaki et al., J. Bacteriol. 172:610–618, 1990); the *B. subtilis* SpoIVC recombinase (Sato et al., J. Bacteriol. 172:1092–1098, 1990); the Hin recombinase (Glasgow et al., J. Biol. Chem. 264:10072–10082, 1989); immunoglobulin recombinases (Malynn et al., Cell 54:453–460, 1988); and the Cin recombinase (Hafter et al., EMBO J. 7:3991–3996, 1988; Hubner et al., J. Molec. Biol. 205:493–500, 1989) can be used. Such alternate systems are discussed by Echols (J. Biol. Chem. 265:14697–14700, 1990), de Villartay (Nature 335:170–174, 1988), Craig (Ann. Rev. Genet. 22:77–105, 1988), Poyart-Salmeron et al. (EMBO J. 8:2425–2433, 1989), Hunger-Bertling et al. (Molec. Cell. Biochem. 92:107–116, 1990), and cregg (Molec. Gen. Genet. 219:320–323, 1989).

Recombinant Expression Vectors and Host Cells

Another aspect of the invention pertains to vectors, preferably expression vectors, containing a nucleic acid comprising a sequence encoding a recombinase and a signal sequence. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into a modified or unmodified viral genome.

A wide range of construct types, both viral and non-viral, can be used to provide the lox site-flanked Cre genes (or regulatory elements) of the invention. In some circumstances, retroviral vectors, such as that described below, provide certain advantages. For example, the placement of a lox site in the retroviral vector of FIG. 1, which is described further below, in the 3' LTR U3 region allows packaging of the retrovirus without excision of the Cre gene. Only after packaging and infection of target eukaryotic cells is the lox site duplicated, by the retroviral reverse transcription process, to flank the recombinase gene and thus permit self-excision. Placement of a single lox site in the 5 ' LTR U5 region accomplishes the same end.

Another advantageous feature of vectors that can be employed in the invention is that provided by the use of non-identical lox sites in a vector containing Cre and a vector containing a target gene. (See, e.g., the vectors used in the experiments described below, in which the vector containing the cre gene includes Lox 511 sites and the target containing the lacZ gene includes lox P sites.) Efficient Cre-based recombination can only occur when the Cre recombinase encounters two identical lox sites (Hoess et al., Nucleic Acids Research 14(5):2287–2300, 1986); the use of two different lox sites, both of which are recognized by Cre, prevents interchromosomal recombination events and large deletions or inversions that could occur if identical lox sites were used in both the recombinase vector and the target.

In other applications, the exogenous target of Cre may have lox sites arrayed in such a manner that the Cre recombinase inverts the sequence between the lox sites, which could, for example, be used to turn off the expression of one gene and turn on the expression of another. In particular, as is discussed above, the Cre protein mediates recombination between two lox sequences, which may be present on the same or different DNA molecules. Because the internal spacer sequence of the lox site is asymmetrical, two lox sites can exhibit directionality relative to one another (Hoess et al., Proc. Natl. Acad. Sci. U.S.A. 81:1026–1029, 1984). Thus, when two sites on the same DNA molecule are in a directly repeated orientation, Cre will excise the DNA between the sites (Abremski et al., Cell 32:1301–1311, 1983). Alternatively, if the sites are inverted with respect to one another, the DNA between them is not excised after recombination, but is simply inverted. Thus, a circular DNA molecule having two lox sites in direct orientation will recombine to produce two smaller circles, while circular molecules having two lox sites in an inverted orientation with respect to one another simply invert the DNA sequences flanked by the lox P sites. For example, a coding sequence for a therapeutic protein could be flanked by inverted lox sites. The promoter/enhancer driving the expression of the gene is not encompassed by the flanking inverted lox site. Infection with a virus carrying a self-excising Cre will invert the coding sequence of the therapeutic protein with respect to its promoter/enhancer, thus terminating expression of the therapeutic protein. Reinfection of the same cells with a virus carrying a self-excising cre will invert the coding sequence of the therapeutic protein again, thus, re-establishing expression.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably, as the plasmid is the most commonly used form of vector. However, the invention is intended to include such other forms of expression vectors, such as viral vectors (e.g., replication defective retroviruses, adenoviruses and adeno-associated viruses), which serve equivalent functions. Particularly useful vectors for this invention include modified retroviral vectors. Examples of such vetors are described in U.S. Pat. Nos. 6,025,192, and 6,200,800, each herein fully incorporated by reference.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The phrase "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., cre/Flp-recombinase nucleic acid molecules, mutants, fusion proteins, etc.).

The recombinant expression vectors of the invention can be designed for expression of a recombinase in either prokaryotic or eukaryotic cells. For example, the recombinase can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using $T_7$ promoter regulatory sequences and $T_7$ polymerase.

In another embodiment, the recombinase expression vector is a yeast expression vector. Examples of vectors for expression in yeast *Saccharomyces cerivisae* include pYepSec1 (Baldari, et al., 1987. *EMBO J.* 6: 229–234), pMFa (Kurjan and Herskowitz, 1982. *Cell* 30: 933–943), pJRY88 (Schultz et al., 1987. *Gene* 54: 113–123), pYES2 (InVitrogen Corporation, San Diego, Calif.), and picZ (InVitrogen Corp, San Diego, Calif.).

Alternatively, the recombinase can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156–2165) and the pVL series (Lucklow and Summers, 1989. *Virology* 170: 31–39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187–195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid), e.g. liver cells. Tissue-specific regulatory elements are known in the art. Non-limiting examples of suitable tissue-specific promoters include the albumin promoter (liver-specific; see, Pinkert, et al., 1987. *Genes Dev.* 1: 268–277), lymphoid-specific promoters (see, Calame and Eaton, 1988. *Adv. Immunol.* 43: 235–275), in particular promoters of T cell receptors (see, Winoto and Baltimore, 1989. *EMBO J.* 8: 729–733) and immunoglobulins (see, Banerji, et al., 1983. *Cell* 33: 729–740; Queen and Baltimore, 1983. *Cell* 33: 741–748), neuron-specific promoters (e.g., the neurofilament promoter; see, Byrne and Ruddle, 1989. *Proc. Natl. Acad. Sci. USA* 86: 5473–5477), pancreas-specific promoters (see, Edlund, et al., 1985. *Science* 230: 912–916), and mammary gland-specific promoters (e.g., milk whey promoter; U.S. Pat. No. 4,873,316 and European Application Publication No. 264,166). Developmentally-regulated promoters are also encompassed, e.g, the murine hox promoters (Kessel and Gruss, 1990. *Science* 249: 374–379) and the α-fetoprotein promoter (see, Campes and Tilghman, 1989. *Genes Dev.* 3: 537–546).

Another aspect of the invention pertains to host cells into which a recombinant expression vector of the intention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, the recombinase containing sequence can be expressed in bacterial cells such as *Escherichia coli*, insect cells, yeast or mammalian cells (such as Chinese hamster ovary cells ((CHO) or COS cells). Other suitable host cells are known to those skilled in the art.

The nucleic acid molecules according to the present invention, may be introduced into host cells or organisms by a variety of methods, including but not limited to transfection techniques, infection with recombinant viral vectors, or as naked DNA, all of which are well known in the art.

A vector containing a nucleic acid molecule of the present invention can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding cre/Flp-recombinase nucleic acid molecule or can be introduced on a separate vector. Cells stably-transfected with the introduced nucleic acid can be identified by drug selection (e.g., cells that have incorporated the selectable marker gene will survive, while the other cells die).

Methods of Use

The self-excising recombinase vectors of the present invention are useful in a wide range of therapeutic, diagnostic, and industrial applications, in which the controlled expression of therapeutic or diagnostic proteins is desired. The vectors of the present invention can also modify cells or organisms to prevent fertility, remove undesirable proteins, or induce desirable gene product expression. Accordingly, the nucleic acid molecules and vectors described herein can be used in one or more of the following methods: (A) methods of treatment (e.g., therapeutic and prophylactic); (B) detection assays (e.g., chromosomal mapping, cell and tissue typing, forensic biology), (C) predictive medicine (e.g., diagnostic assays, prognostic assays, monitoring clinical trials, and pharmacogenomics); (D) production of therapeutic molecules either from cells or whole animals; (E) production of agricultural products; and (F) prevention of spread or theft of transgenic animals or plants.

Research Reagents

Vectors of the invention that are useful as research reagents can include a recombinase gene flanked by signal sequences recognized by the expressed recombinase, or a recombinase gene having a regulatory element that is flanked by such sequences. These constructs are useful in a wide range of research contexts (see, e.g., Sauer, Methods: A Companion to Methods in Enzymology 14:381–392, 1998). For example, there are many instances in which a researcher may wish to study the effect of transient expression of a recombinant protein on cultured cells. The researcher thus may wish to study the cells before, during, and following such expression. The conventional Cre-lox system can be used to limit expression of a recombinant protein in cell culture, but the toxicity of Cre can confound post-expression study of the cells. The vectors of the invention can be used to limit the expression of a recombinant protein in cell culture, while avoiding, because of the self-excision of Cre (or a Cre regulatory element), the toxicity of Cre. Furthermore, lox sites can be positioned in such a way that recombination activates, rather than inactivates, the expression of a target gene, and the invention can be used in this context as well. For example, the lox sites can flank a negative regulatory element of a target gene or an element that is inserted by artifice into a gene to block its expression (e.g., a polyadenylation signal that is inserted between a promoter and a coding sequence; see below). After the introduction of Cre, the target gene is expressed and Cre expression is terminated, thus, allowing the cell to express the target gene without the toxicity of Cre.

There are many possible uses for the research reagents of the invention, in which a Cre or other recombinase gene (or a regulatory element thereof) is flanked by lox or other recombinase-recognized sites. One example is in the study of cultured tumor cells that are potentially affected by the expression of a tumor suppressor protein, such as p53 or the retinoblastoma (Rb) protein. A genetic construct in which the tumor suppressor gene (or a regulatory element thereof) is flanked by lox sites is introduced into the tumor cell culture, be it by homologous recombination or otherwise. The cells are also transfected or infected with a construct in which Cre (or a regulatory element thereof) is flanked by lox sites. The tumor suppressor protein is expressed for a limited period of time, after which it (or its regulatory element) is excised by the co-expressed Cre protein, which also excises the Cre gene itself (or a Cre regulatory element), avoiding undue Cre toxicity. The researcher thus is able to observe the cultured tumor cells prior to tumor suppressor protein expression, during tumor suppressor protein expression, and after tumor suppressor protein expression has ceased, without the confounding influence of Cre toxicity in the cell culture.

Therapeutic Applications

The present invention provides for both prophylactic and therapeutic methods of treating a subject at risk of, susceptible to, or suffering from a disease or disorder associated with the selected target gene, or its absence or presence. Controlled addition or elimination of target gene expression can be achieved in the absence of complications of continued recombinase expression. These therapeutic methods will be discussed more fully below.

In one example of such an application, the recombinase gene is under the control of a promoter that is inducible by a small molecule. The recombinase gene and a therapeutic or diagnostic target gene, the expression of which it is desired to be limited in duration, can be present in, for example, a tissue that is transplanted into a patient. The small molecule can be administered to the patient to effect expression of the recombinase, which, over time, inactivates expression of the target gene and itself.

For example, a person requiring a bone marrow transplant can receive marrow that has been transduced with a gene encoding a cytokine(s) or other factor(s) that promote rapid and full engraftment. The genes encoding the cytokine (e.g., GM-CSF) or other factor, or regulatory elements thereof, are flanked by lox sites. The recombinase gene, which is also flanked by lox sites, is under the control of a promoter that is inducible by a small molecule that can be administered to the patient at will. After complete engraftment, the small molecule inducer can be administered to the patient, eliminating further unnecessary and potentially harmful bone marrow stimulation by the cytokine or other factor, and the potential toxicity or antigenicity of the recombinase is avoided.

A second example of this type of application is the modification of transplanted tissue by an anti-apoptotic gene to promote its engraftment. Such modification may be desirable in the short term to promote successful transplantation, but might be harmful in the long term, by, for example, raising the probability of tumorigenic transformation of transplanted cells. The anti-apoptotic gene could be flanked by recombinase signal sequences, and, either within the same signal sequences or flanked by its own recombinase signal sequences, the recombinase can be present in a configuration that makes it inducible by administration of a small molecule. After the critical period for engraftment, the small molecule inducer can be administered, removing the possibly harmful anti-apoptotic gene, with the potential complications caused by prolonged or high level recombinase expression minimized by self-deletion of the recombinase.

Figure 2:
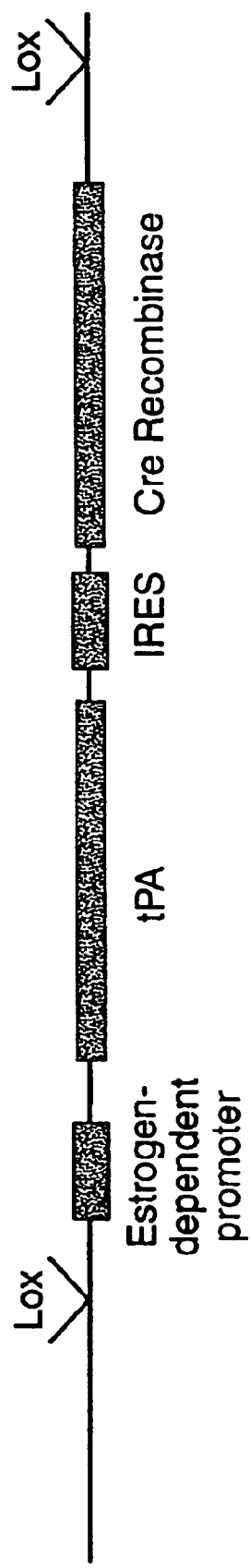
FIG. 2 is a schematic representation of a vector of the invention, in which both the Cre gene and a gene encoding a therapeutic protein, tissue plasminogen activator (tPA), are flanked by lox sites.

An example of a genetic construct of the invention that is useful in controlled therapeutic protein administration is shown schematically in FIG. 2. The vector is constructed such that transcription generates a bicistronic messenger RNA encoding the cre recombinase and the clot-dissolving protein tPA; both coding regions are flanked, in the vector, by lox sites recognized by cre. Upstream of both coding regions is an inducible promoter, activatable by estrogen.

The vector can be injected into a site, e.g., the muscle of the arm or leg, of a male patient who is at risk for myocardial infarction and has no circulating estrogen. The patient, who may be traveling to a location where prompt medical attention is not likely to be available, carries with him a syringe containing estrogen, the molecule that initiates transcription of the genetic construct already residing in the patient's body. When the patient experiences symptoms of a myocardial infarction, he injects the estrogen into his body, effecting initiation of transcription of the bicistronic coding region. This method can also employ a promoter that is inducible by a small molecule or a hormone, such as ecdysone, which would be administered to the patient (male or female) to initiate transcription of the bicistronic coding region.

Although tPA and other drugs perform lifesaving functions, it is often necessary that the dosage and duration of expression be limited. tPA, for example, if expressed in large amounts or for too long a period of a time, can cause bleeding complications. In the present example, the cre that is co-expressed with tPA acts, after the desired tPA expression level has been reached, to excise the tPA gene from the construct, stopping its expression. At the same time, cre excises the cre gene itself, so that not only is tPA expression halted, but potentially toxic cre expression ceases as well.

As is mentioned above, the vectors used in the therapeutic schemes of the invention can have a wide variety of configurations. For example, rather than providing the cre gene and the therapeutic protein gene on the same vector, the genes can be provided on two separate vectors, each with appropriately placed lox sites. Instead of cre and its corresponding lox target sites, any site specific recombinase and its target sites may be used in the method.

The therapeutic concept of the invention can be used to control the administration of any therapeutic protein, including single chain monoclonal antibodies, which are useful as both active therapeutics (e.g., to target tumors) and as passive immunotherapeutic agents targeting pathogens, including viruses and bacteria. In addition, the methods of the invention can be used to control the gene dose delivered to patients in gene therapy regimens, including those in which gene expression is not involved, e.g., antisense therapy. For example, the methods can be used to reverse part or all of a gene therapy intervention, e.g., in the case of unanticipated toxicity. One could envision an adenovirus designed to correct a genetic defect, that, in addition to the gene that corrects the defect, encodes a self-excising inducible cre and has lox sites flanking possible immunogenic coding regions of the adenovirus. In the case of severe allergy to the virus, cre could be induced by a small molecule, and the allergens removed, while the gene correcting the genetic defect is still expressed. Similarly, the methods can be used to activate part or all of a gene therapy intervention. In either case, the continued presence, potential toxicity, or potential immunogenicity of cre is avoided.

Transgenic Animals

The host cells of the invention can also be used to produce non-human transgenic animals. For example, in one embodiment, a host cell of the invention is a fertilized oocyte or an embryonic stem cell into which recombinase nucleic acid molecule-coding sequences have been introduced. These host cells can then be used to create non-human transgenic animals in which exogenous nucleic acids sequences have been introduced into their genome or homologous recombinant animals in which endogenous sequences have been altered. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc.

A transgene is exogenous DNA that is integrated into the genome of a cell from which a transgenic animal develops and that remains in the genome of the mature animal, thereby directing the expression of an encoded gene product in one or more cell types, e.g. liver, or tissues of the transgenic animal. As used herein, a "homologous recombinant animal" is a non-human animal, preferably a mammal, more preferably a mouse, in which an endogenous nucleic acid molecule gene has been altered by homologous recombination between the endogenous gene and an exogenous DNA molecule introduced into a cell of the animal, e.g., an embryonic cell of the animal, prior to development of the animal.

A transgenic animal of the invention can be created by introducing recombinase nucleic acid molecule-encoding nucleic acid into the male pronuclei of a fertilized oocyte (e.g., by micro-injection, retroviral infection) and allowing the oocyte to develop in a pseudopregnant female foster animal. Intronic sequences and polyadenylation signals can also be included in the transgene to increase the efficiency of expression of the transgene, or to eliminate potential inappropriate expression of the recombinase in *E. coli* during cloning (see above). A tissue-specific regulatory sequence(s) can be operably-linked to the recombinase nucleic acid molecule transgene to direct expression of the protein to particular cells, e.g. liver cells. Methods for generating transgenic animals via embryo manipulation and micro-injection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the cre/Flp-recombinase nucleic acid molecule transgene in its genome and/or expression of the cre/Flp-recombinase nucleic acid molecule mRNA in tissues or cells of the animals. A transgenic founder animal can then be used to breed additional animals carrying the transgene. Moreover, transgenic animals carrying a transgene-encoding cre/Flp-recombinase nucleic acid molecule can further be bred to other transgenic animals carrying other transgenes.

To create a homologous recombinant animal, a vector is prepared which contains at least a portion of the target nucleic acid molecule into which a deletion, addition or substitution has been introduced to thereby alter the target nucleic acid molecule, to, for example, introduce lox sites. The vector is then introduced into an embryonic stem cell line (e.g., by electroporation) and cells in which the introduced nucleic acid has homologously-recombined with the target nucleic acid molecule are selected. See, e.g., Li, et al., 1992. *Cell* 69: 915. The selected cells are then microinjected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. *Curr. Opin. Biotechnol.* 2: 823–829; PCT International Publication Nos.: WO 90/11354; WO 91/01140; WO 92/0968; and WO 93/04169.

Clones of the non-human transgenic animals described herein can also be produced according to the methods described in Wilmut, et al., 1997. *Nature* 385: 810–813. In brief, a cell (e.g., a somatic cell) from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

In another aspect, the vectors of the invention can be used to limit or control the production of useful proteins, such as tPA, in targeted secretions (e.g., milk and urine) of transgenic animals, such as cattle and goats, both of which are currently used as recombinant protein "factories." The invention can be used in conjunction with current standard genetic constructs used to produce transgenic mammals (e.g., cattle, goats, and pigs) that make tPA, β-interferon, and other therapeutically important proteins in the milk or urine of the mammals (e.g., by companies such as Genzyme Transgenics Corporation, Cambridge, Mass.). In these animals, the gene for a desired protein is placed under the control of a constitutively active or inducible promoter that is specific for either urinary epithelium (if the protein is to be produced in urine) or mammary tissue (if the protein is to be produced in milk) of the mammal. Conventional urine-specific promoters include the uromodulin and uroplakin promoters, while conventional milk-specific promoters include the casein promoters and the whey acid protein promoter. The construct also includes a leader sequence, which effects secretion of the expressed protein. (Such constructs and their use are described, e.g., in Meade, U.S. Pat. Nos. 5,849,992 and 5,750,172.) Conventional microinjection or other techniques are used to introduce the genetic construct into the mammalian embryo, which is then implanted into a pseudo-pregnant female, in which it develops to term and is eventually born and allowed to mature into an animal that secretes the desired protein into its urine or milk.

Currently, if a female mammal that produces a desired protein in its milk is to be used for another purpose, e.g., breeding, there is no satisfactory mechanism for shutting down production of the therapeutic protein in the milk of the mammal. Thus, it is not currently practical to breed one of these female transgenic goats and allow it to nurse its offspring, because the milk contains the therapeutic protein, rendering it unacceptable food for the newborn mammals. Further, breeding could be compromised by continuous production of the therapeutic protein.

The invention can be used to safely shut down production of the therapeutic protein at any time. In one example, the transgene encoding the therapeutic protein is flanked by lox sites, and the genetic construct includes the cre gene, also flanked by lox sites. The cre gene is positioned downstream from an inducible promoter, e.g., a promoter that is activated by testosterone or a small molecule. The animal that matures from the transgenic embryo thus contains, in all of its cells, including the milk-secreting cells lining the mammary glands, both the therapeutic protein construct, flanked by lox sites, and the cre gene, flanked by lox sites.

After the transgenic mammal has produced the therapeutic protein in its milk for a sufficient period of time, and it is desired that production cease, a syringe containing testosterone or the small molecule is inserted into the teat of the animal. The administered agent enters the milk-producing cells lining the mammary gland, initiating transcription of the cre gene. The expressed cre recombinase excises the gene for the therapeutic protein in the milk-producing cells, stopping expression of that protein. The cre recombinase excises the cre gene, preventing cre toxicity in the milk-producing cells.

Alternatively, for example, the invention can be used to activate expression of a foreign gene in a transgenic animal at an appropriate time. Similar to the example provided below, a gene encoding a therapeutic protein is under the control of a mammary-specific promoter, but between the promoter and the protein coding sequence is a polyadenylation sequence flanked by lox P sites. A second construct includes the cre recombinase gene under the control of a tetracycline-inducible promoter and flanked by Lox 511 sites. After completion of breeding and nursing, or other activities during which transgene expression is undesirable, the animal can be given tetracycline, which activates expression of the transgene by deletion of the polyadenylation site. The cre-bearing construct is also deleted, thus preventing any potential toxicity or antigenicity of cre. The animal's milk is then a source of the recombinant protein.

The nucleic acid molecules and methods of the invention can also be used to generate animal (e.g., mouse) model "knock outs," which can be used in many applications in research and protein production (see below). As a specific example, the invention can be used in the generation of animal models having tissue-specific gene knock outs. To generate such animals, a target gene, or a portion of a target gene, is flanked by lox sites by using homologous recombination in the germ line, and the Cre recombinase gene is added to the germ line under the control of a tissue-specific promoter. The resulting animal deletes the target gene only in tissues that express the Cre recombinase, thereby bypassing unwanted effects that may, for example, kill or disable the animal during embryogenesis or lead to difficulties in other tissues in the adult. The invention, in this context, provides for the inactivation of continued Cre expression in those tissues in which the target is deleted, thereby avoiding toxicity, immunogenicity, and other potential complications resulting from continued recombinase expression.

For example, to study the metabolism of a drug by a particular drug metabolism gene in the liver, but not the kidney, it may be desirable to knock out expression of the gene in the liver, but not in the kidney. Thus, the Cre gene (or a regulatory element thereof) can be flanked by lox 511 or lox P sites that will not affect normal expression, and can be introduced as a transgene under the control of the liver-specific promoter, such as the albumin promoter. The drug metabolism gene is flanked by lox P sites introduced by homologous recombination in the germ line. Because of the tissue-specific promoter controlling cre expression, the drug metabolism gene will be deleted only in the liver, and not in the kidney or elsewhere in the resulting animal. To avoid Cre toxicity or other unwanted Cre effects, the Cre expression cassette contains lox sites, thus inactivating expression of itself wherever it is expressed, as well as the intended target.

In another application, deletion of the recombinase gene can be used to position a marker gene, such as GFP or β-galactosidase, in proximity to the promoter that was driving expression of Cre, thus marking cells that have undergone Cre-mediated self-excision and deletion of the target as well. In addition to knocking out coding sequences in animal models, the nucleic acid molecules and methods of the invention can be used to delete positive or negative regulatory elements of genes in such animal models, as is described above.

Transgenic Plants

As is noted above, the invention also finds utility in transgenic plants, in which the cells of a plant express a transgene (e.g., a gene encoding a protein conferring pathogen resistance to a plant, or a gene imparting superior growth properties to a plant) that includes signal sequences recognized by a recombinase (e.g., cre). According to the invention, cells of such a plant also include a recombinase gene (e.g., cre), that includes recombinase target sites (e.g., lox sites, in the case of cre) positioned so that, upon production of a certain level of recombinase, the sites are recognized by the recombinase, resulting in the inactivation of recombinase expression. The expressed cre acts on the transgene to modulate (e.g., activate or inactivate) its expression, depending on the construct used and the desired effect. Preferably, an inducible promoter is used to drive cre expression in such plants. For example, a promoter that is activated at a particular stage of plant development can be used, and thus cause cre expression, followed by cre inactivation, in the plant a particular stage of development. A promoter that is inducible by an agent to which a plant can be exposed (e.g., a compound that can be introduced into a plant by including the compound in water that is used to water the plant, a compound that is sprayed onto the plant, or an energy source, such as heat or light) can also be used with the cre gene. It may be desirable to use a system, such as the cre-lox system, to delete all foreign sequences (including recombinase sequences) from such a plant, for example, prior to harvesting.

In another example, which is described in further detail below, the cells of first and second different tissues of a plant express a transgene (e.g., a gene encoding a protein conferring pathogen resistance) that includes signal sequences recognized by a recombinase. A nucleic acid molecule that includes the recombinase gene and signal sequences recognized by the recombinase is expressed in cells of edible parts of the plant, but not cells of the inedible portions. Thus, the recombinase expressed in the edible portions of the plant deletes or disables the potentially toxic pathogen resistance or other peptide, as well as the recombinase itself. The vast majority of exogenous DNA sequences can be eliminated from the edible portion in this method, including the recombinase gene.

A number of pathogen-derived proteins are currently expressed in plants to render the plants resistant to those pathogens. Among many examples, the coat protein of the RNA virus grapevine leafroll virus has been expressed in grape plants, rendering them resistant to the virus. A problem with this approach is that it leaves a residue of potentially toxic or anti genic viral coat protein in the edible parts of the plants, i.e., the grapes.

According to the invention, cultured grape plant tissue is transfected with a genetic construct in which the gene for the viral coat protein is flanked by lox sites. Transfection is carried out according to conventional methods, e.g., using *A. tumefaciens* or a gene gun, such that when a whole plant is grown from the cultured cells, all of the tissues contain the coat protein construct, as is standard practice. The cultured grape tissue cells are also transfected with a second transgene, which can be part of the same construct on which the coat protein gene is carried, or a separate construct, containing the cre gene flanked by lox sites. The cre gene is positioned downstream from, and under the transcriptional control of, an inducible promoter that is activated by a compound found in the grapes but not in the remainder of the plants, e.g., one of the enzymes in the fructose production pathway. Thus, although all of the cells in the mature grape plant will contain the cre construct, the cre recombinase will be expressed only in the grapes of the plant, where fructose is made. Thus, in the grapes, but not the inedible portions of the grape plant, cre excises the coat protein gene, as well as the cre gene itself, minimizing toxicity and other undesirable effects in the grapes of both the coat protein and cre, while leaving unaffected the coat protein-mediated pathogen resistance in the inedible portions of the plant.

Libraries

Another research application of the invention involves the creation of libraries of cells containing lox sites scattered throughout the genome. The self-excising, Cre-bearing retroviruses leave behind, at the site of integration, a single LTR with a lox site embedded within it. Introduction of a second lox site into the genome of a cell containing such an LTR, by any means, including reinfection with the original retrovirus, can result in the generation of large chromosomal deletions or rearrangements upon re-expression of Cre. If done in embryonic stem cells, animals bearing these deletions can be generated as well. Such a collection of defined chromosomal deletions, whether in cultured cells or animals, can be used, for example, in mapping the location of various functions, and in uncovering the functions of, for example, tumor suppressor genes. In addition to higher eukaryotic cells and plants, this type of deletional mapping can be used in BACS in *E. coli* or YACS in yeast. (See, e.g., Ramírez-Solis et al., Nature 378:720–724, 1995, for a general description of generation of chromosomal rearrangements in mice involving the use of the Cre-lox system.)

Multiple Self-Excising Recombinases with Different Target Sequences

A further application of the vectors and methods of the invention, which has use in research, therapy, and diagnostics, involves the use of multiple self-excising recombinases with different target sequences, applied at the same time or sequentially, to control a vast array of sequential or more complicated gene expression events. For example, a first recombinase, such as Cre, can be used to activate a target gene and self-excise, and then a second recombinase, such as flp, can be used to inactivate the same target gene and self-excise. Also, to set up a pulse of expression, a first recombinase, such as Cre, can be used to activate the expression of a gene, e.g., tPA, as well as a second recombinase, such as flp, as well as self-excising. Flp would then terminate expression of tPA, and also self-excise. Thus, the therapeutic, diagnostic and industrial methods of the invention can employ multiple recombinases and target sequences, to obtain higher level control of a gene expression pathway.

Industrial Applications

The invention also finds utility in applications involving the manufacture of proteins or other molecules in which cells are used to generate the substance of interest. Often, pharmaceutical or other concerns use large volume fermenters containing large numbers of cells to produce a substance. As an example, growth factors that increase the speed of growth or density tolerated of cells in such a fermenter may be desirable at one phase of growth only; such a factor could be activated or deleted at the appropriate time during growth by inducing recombinase action. Further undesirable activity of the recombinase, such as toxicity or growth inhibition would be eliminated by self-excision of the recombinase.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting.

The invention will be further illustrated in the following non-limiting examples.

EXAMPLES

Example 1

Cre Recombinase Activity Results in Cellular Toxicity

Figure 4A:
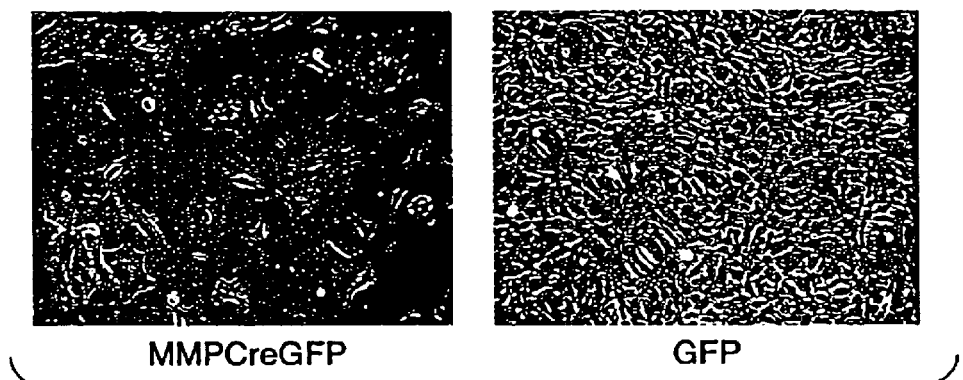
FIGS. 4A–C show cre recombinase toxicity in tissue culture cells.
Figure 4B:
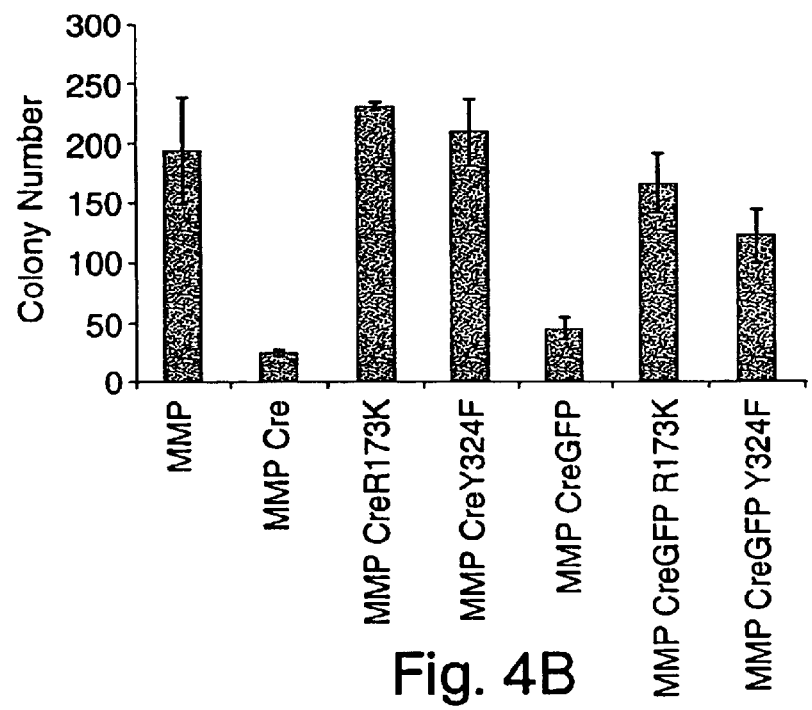

While characterizing retroviral vectors that express the cre recombinase, we noted that cells infected with these vectors ceased to proliferate and displayed obvious phenotypic changes five to ten days after infection. As shown in FIG. 4A; a human embryonic kidney cell line revealed decreased growth and abnormal morphology after infection with a virus encoding a cre-GFP fusion protein but not with a virus encoding GFP alone. A derivative of 293 cells, 293×Lac, was infected with either MMPcreGFP (left) or a virus encoding GFP (right). The cells were passaged identically for nine days after infection and photographed.

Cells expressing the cre-GFP fusion protein ceased to proliferate and often spread out on the dish, displaying a greatly increased cytoplasmic to nuclear ratio. Moreover, many syncytia were observed. No such changes were observed in cells infected with the virus expressing GFP alone. In addition to 293xLac cells, unmodified primary mouse embryo fibroblasts (MEFs), NIH 3T3 cells, and the human osteosarcoma cell line, U2OS, all behaved in a similar manner, and a virus encoding the cre recombinase alone (not fused to GFP) also caused the same changes in each of these cell lines (data not shown). Thus, the toxic effect of the cre recombinase is not cell-specific or GFP-dependent; furthermore, it does not require the presence of exogenous lox sites.

Figure 4C:
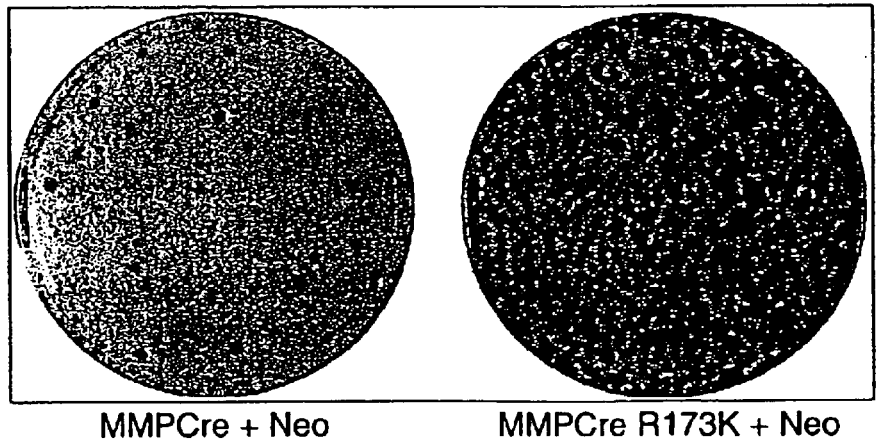

To investigate this toxicity further, a series of retroviral vectors expressing two mutant alleles of the cre recombinase, R173K and Y324F, were constructed, either alone or as GFP fusion proteins. These mutant cre alleles are known to bind to lox sites but cannot cleave DNA (Abremski and Hoess, 1992; Guo et al., 1999; Wierzbicki et al., 1987). These expression vectors or the empty retroviral vector were transfected into unmodified NIH 3T3 cells (free of any introduced lox sites) together with pPNT, a plasmid encoding G418 resistance (Tybulewicz et al., 1991). After G418 selection, antibiotic-resistant colonies were counted. As shown in FIG. 1B, vectors expressing either cre or the cre-GFP fusion protein caused a significant decrease in the number of G418-resistant colonies compared to vectors encoding either of the mutant cre proteins, or to empty vector. In addition, similar colony numbers were observed when the empty expression vector and any of the cre mutant alleles were transfected. Typical cultures from this type of experiment are shown in FIG. 4C. Transient transfection of these vectors into 293T cells followed by western analysis for cre expression suggested that cre and the two mutants, R173K and Y324F, were equally stable, and, when fused to GFP they were expressed equivalently (data not shown). Taken together, these results demonstrate that active cre recombinase can cause significant toxicity when introduced into a variety of cell types, that this toxicity is dependent upon the DNA cleavage function of the recombinase, and that it occurs in cells lacking ectopically introduced lox sites.

Figure 5A:
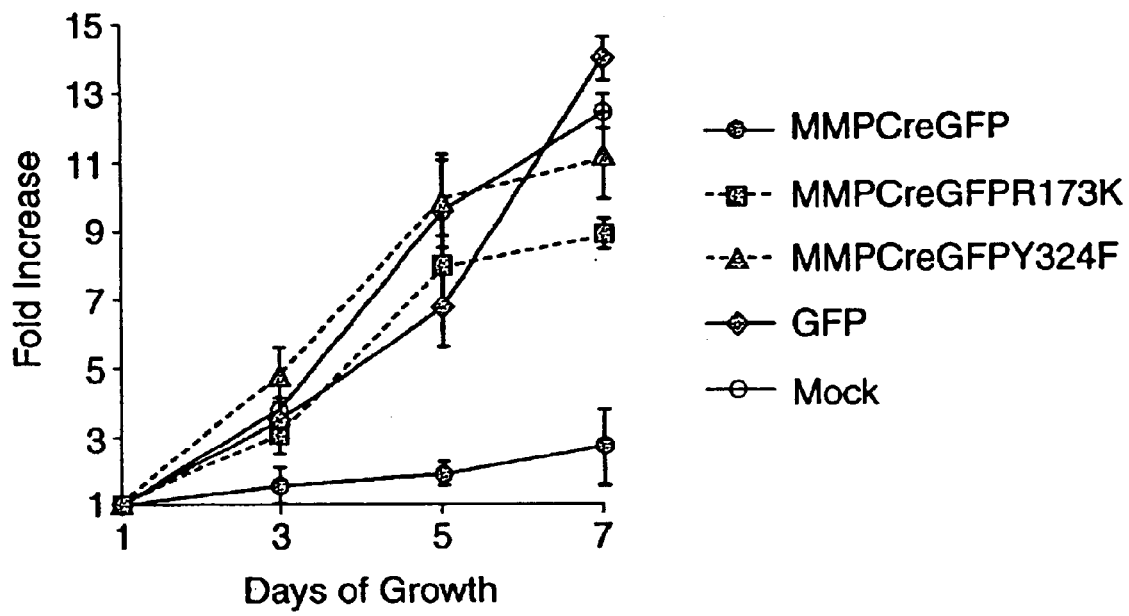
FIGS. 5A and B depict that cre recombinase causes growth retardation in mouse embryo fibroblasts (MEFs).

Analysis of the proliferative behavior of mouse embryo fibroblasts after infection with retroviruses encoding cre-GFP fusion proteins again reflected the effects of cre toxicity. A single plate of early passage, wild-type (wt) MEFs with no ectopically introduced lox sites was split, and the replicate plates were infected with retroviruses encoding wt or mutant cre-GFP fusion proteins, GFP alone, or they were mock-infected. All cultures were serially passaged for five days and then seeded at equal density. The next day and every other day thereafter for seven days, viable cell number was determined. As shown in FIG. 5A, the proliferation of MEFs infected with a virus encoding wt creGFP fusion protein was significantly retarded compared to mock-infected MEFs, MEFs infected with a GFP-encoding retrovirus, or MEFs synthesizing mutant cre-GFP fusion proteins that bind lox sites but do not cleave them. Remarkably, MEFs infected with the wt cre-GFP bearing retrovirus barely proliferated at all, and, in some experiments, underwent a decrease in cell number (FIG. 5A and data not shown). Again, there was no significant difference in the proliferation rate of mock-infected MEFs and MEFs infected with retroviruses expressing mutant cre-GFP fusion proteins, suggesting that the toxicity observed depends upon the DNA strand cleavage activity of cre. To check the expression levels of creGFP and mutants thereof, a western blot of total cell protein was prepared from cells on day two of the proliferation assay shown in FIG. 5A and probed with anti-cre antibody (FIG. 5B, lanes 1–3). cre-GFP and the two mutant cre-GFP proteins were expressed at similar levels, eliminating the possibility that widely differing expression levels of the relevant creGFP alleles caused the observed differences in cell proliferation.

Example 2

A Self-Excising (Hit and Run) Vector Efficiently Deletes Itself and a Target DNA Sequence Situated in Trans Given these results, we hypothesized that limiting the intensity and duration of cre expression to the minimum level necessary for excision of a target sequence might reduce or eliminate the observed toxicity. To this end, a retrovirus that incorporates a negative feedback loop to regulate cre expression was constructed. This regulation was accomplished by flanking the gene encoding the cre recombinase by lox sites. The expectation was that, upon expression, the cre recombinase would excise the gene directing its own synthesis once the critical level of expression required for excision was reached. In assessing the properties of the self-excising cre expression vector, the important questions were whether the cre concentration realized in this unusual situation is sufficient to excise a target elsewhere in the genome, and, if so, whether further cre expression also terminates at that point.

Figure 6:
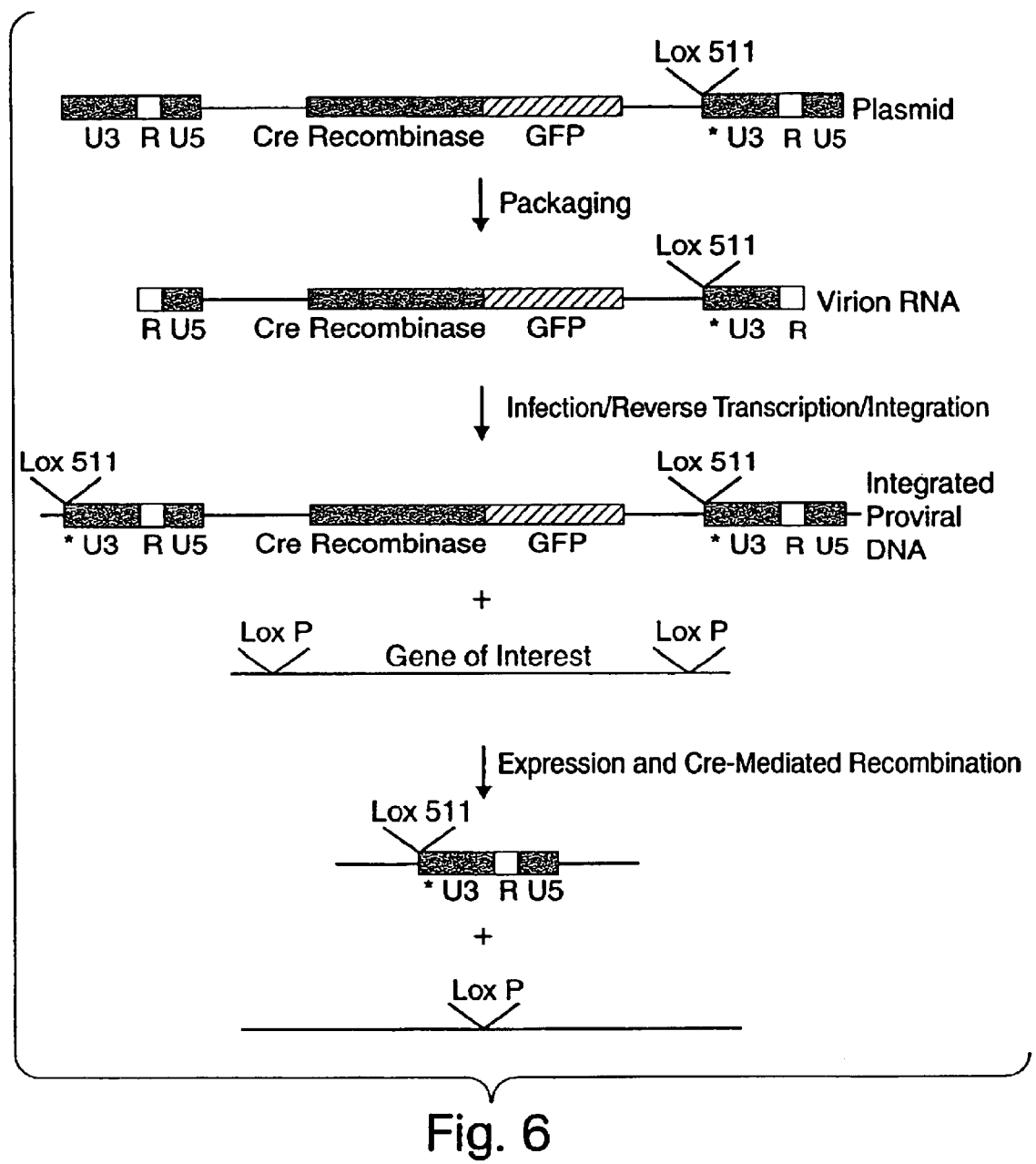
FIG. 6 shows the mechanism of action of HR-MMPcreGFP (Hit and Run), a self-excising, cre-encoding, retroviral vector.

The simplest embodiment of this concept in a retroviral vector would be to flank the gene encoding cre with lox sites. However, retroviral vectors are DNA plasmids (proviruses) that must be transfected into cells to allow production and packaging of the virion RNA. Because the virion RNA genome itself is a functional mRNA, the cre recombinase would act upon the vector DNA during the viral packaging phase of vector production and delete the cre recombinase coding sequence. To avoid this problem, we took advantage of the fact that the U3 region of the 3' LTR of a retroviral vector is the template for production of both U3 regions in the provirus that results after infection of a target cell (see FIG. 6) (among the relevant references are Gilboa et al., 1979a; Gilboa et al., 1979b; Shank et al., 1978). Because the packaging step does not entail duplication of the U3 lox site, this design allows packaging of the newly synthesized virion RNA without excision of the cre gene. When the packaged virus infects a suitable target cell, reverse transcription and proviral generation occur, resulting in U3 lox site duplication (FIG. 6). The latter permits the development of a negative feedback loop in the target cell, because the newly integrated cre gene, now flanked by two lox sites, can promote its own excision (FIG. 6). A virus with this characteristic can be viewed as having 'hit and run' properties.

There is a previous report of a self-deleting cre cassette constructed for other purposes. This cassette is different from the one described here in that it expresses cre only during spermatogenesis and also contains a ubiquitously expressed selectable marker. The intent in that study was to use the cassette first to select an ES cell that has undergone a desired homologous integration event using the ubiquitously expressed selectable marker, and then to delete that same selectable marker from the germline of the mouse subsequently derived from that ES cell (Bunting et al., 1999). In the present work, the aim was to create an efficient, general purpose vector that would support cre/lox-mediated recombination in somatic cells, including those in culture, while avoiding the toxicity described above.

Referring to FIG. 1, we constructed retroviral vectors that encodes Cre, fused to the jellyfish protein Green Fluorescent Protein (GFP), with and without lox sites. (See, e.g., Gagneten et al., Nucleic Acids Research 25(16):3326–3331, 1997, for a description of an additional GFP/Cre fusion that can be used in the invention.) To create a vector lacking lox sites, Cre coding sequence was the template for a PCR reaction with primers 1 and 2 (see below), such that an NcoI site was created at the first codon of Cre, and SfiI, NotI, and BclI sites were appended to the C-terminus of the Cre open reading frame. The PCR product was cut with NcoI and BCII, and ligated between the NcoI site and the BamHI site of the retroviral vector, pMMP. This construct (pMMPCrepolylinker) was cut with SfiI, the ends blunted, and then cut with NotI. Into this cleaved construct was inserted a fragment encoding the green fluorescent protein, GFP, prepared from the plasmid pEF/Myc/Nuc/GFP (Invitrogen) by digestion with SfiI, blunting of the resulting ends, and then digestion with NotI. The resulting plasmid, pMMPCreGFP, encodes a retrovirus that expresses a fusion protein consisting of the Cre recombinase at the N-terminus and GFP at the C-terminus.

To construct a vector including a lox site, HR-MMPCreGFP(FIG. 1), which is a retrovirus with a self-excising cre-GFP fusion, the retrovirus described above, PMMPCreGFP, served as a template in a PCR reaction with primers 3 and 4 (see below), such that the PCR product contained the 3' end of the Cre coding sequence including the XhoI site, GFP, and the 3' LTR through the NheI site. Primer 4 was designed to introduce a unique StuI site and a Lox 511 site 5' to the NheI site. This PCR product was cut with NheI and XhoI to create fragment 1. Fragment 2 resulted from the cleavage of MMPCreGFP with EcoRI and NheI and contained the remainder of the 3' LTR and the 3' region flanking the provirus. Fragment 3 resulted from the cleavage of pMMPCreGFP with EcoRI and XhoI, and constituted the plasmid backbone, 5' LTR, 5' untranslated region, and Cre coding sequence to the XhoI site. Fragments 1, 2, and 3 were ligated together in a three-part ligation to create HR-MMPCreGFP (FIG. 1).

```
                                  (SEQ ID NO:3)
Primer 1: GGG CAC GAC CAT GGC CAA TTT ACT GAC
CGT ACA CC (SEQ ID NO:4)
Primer 2: CGC CCT GAT CAG CTA TTG TCT TCC TAT
GCG GCC GCG GGT TTA ATG GCC AAG GTG GCC CCA
TCG CCA TCT TCC AGC AGG CG (SEQ ID NO:5)
Primer 3: GTC AAG TTT GAA GGT GAT ACC C (SEQ ID NO:6)
Primer 4: GGT AGC TAG CAG GCC TAT AAC TTC GTA
TAA TGT ATA CTA TAC GAA GTT ATC TAG CTT GCC AAA
CCT ACA GGT G
```

The construct of FIG. 1 was co-transfected, with viral packaging functions, into the highly tranfectible cell line 293T. Virus was harvested from the cell culture supernatants. This virus was used to infect a cultured tumor cell line. Retroviral infection followed, with the retroviral reverse transcription process using the U3 region of the 3' LTR as a template for the creation of the U3 region of both the 5' and 3' LTRs of the resulting integrated provirus. Thus, in the integrated provirus, the Cre gene is flanked by lox sites, as is described above.

Figure 3:
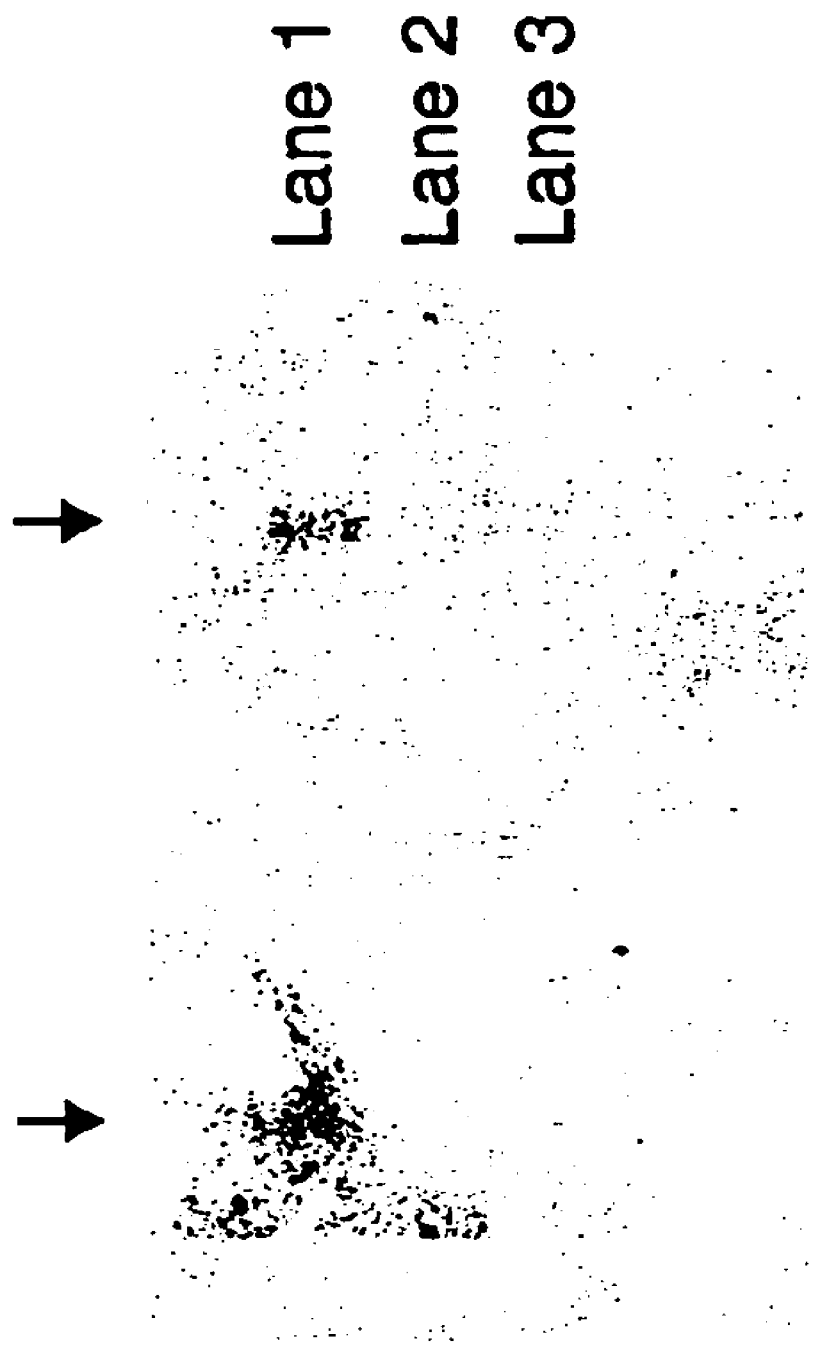
FIG. 3 shows Southern blot of DNA from an indicator cell line infected with Cre recombinase-encoding viruses. The probe is specific for cre. Lane 1 is DNA from cells infected with a virus encoding a Cre-GFP fusion, but no lox sites; lane 2 is DNA from cells infected with a virus encoding a Cre-GFP fusion and a lox 511 site in U3 (see FIG. 1), and lane 3 is DNA from mock-infected cells. The restriction digestion was carried out with EcoRV in all cases. The arrows indicate the sizes of the expected restriction products. The absence of bands in lane 2 indicates highly efficient self-excision; the indicator cell lines corresponding to lanes 1 and 2 had equivalent numbers of β-galactosidase-positive cells, indicating that both viruses were highly efficient at Cre-mediated recombination at a target elsewhere in the genome.

In addition to the viral vector of FIG. 1, the infected cells contained a transfected plasmid in which the lacZ gene, encoding the blue-color-generating enzyme β-galactosidase, was separated from its promoter by a polyadenylation signal flanked by lox P sites. The cells produced insufficient β-galactosidase to be blue in the absence of recombination, but the Cre-GFP fusion quickly excised the polyadenylation sequence, and excised the Cre-GFP gene as well, avoiding significant toxicity that otherwise would have resulted from Cre expression. Blue cells resulted, indicating excision of the target polyadenylation signal. In control cells, in which the Cre-GFP construct was not flanked by lox sites, blue cells resulted, but then ceased proliferating due to Cre toxicity, indicating that excision of Cre, as in the test cells, was necessary to avoid this toxicity. Southern blot analysis confirmed excision of the Cre sequences in the experimental cells, but not in the control cells (FIG. 3).

The lox site is a 34 base pair sequence consisting of two 13 base pair inverted repeats surrounding a core of 8 base pairs. The recombinase tolerates considerable sequence diversity within the core region. However, any two lox sites must have similar core sequences for the recombinase to utilize them efficiently in a single recombination reaction (Hoess et al., 1986). We took advantage of this property of cre to avoid the unlikely possibility that recombination would occur between a proviral lox site and lox sites introduced elsewhere in the genome of an infected cell. Specifically, lox 511, which differs from the widely used lox P site by a point mutation in the core region, was used for construction of the self-excising cre retrovirus. It will not recombine efficiently with a lox P site, but, when paired with another lox 511 site, remains an efficient substrate for cre-mediated recombination (Hoess et al., 1986; Lee and Saito, 1998). The design and potential action of this self-excising cre recombinase-encoding virus, termed HR-MMPcreGFP (i.e. Hit and Run virus encoding cre-GFP), is shown in FIG. 6.

As an initial test of the efficiency of HR-MMPcreGFP at deleting a target sequence with flanking lox sites, 293×Lac cells (a kind gift of Drs. R. Wells and S. Orkin) were infected in parallel with this virus and with MMPcreGFP, an identical virus except for the absence of a lox 511 site in its 3' LTR. 293×Lac cells are 293 cells stably transfected with a plasmid consisting of the CMV immediate early promoter followed by a lox P site, then a number of "stopper" features [including an SV40 polyadenylation site, a false translation initiation signal, and a splice donor designed to prevent the expression of any open reading frame downstream (Lakso et al., 1992)], another lox P site, followed by the gene encoding β-galactosidase. This cell line does not produce appreciable β-galactosidase until cre-mediated recombination between the lox P sites removes the "stopper" sequences, thus permitting β-galactosidase to be produced.

Figure 7A:
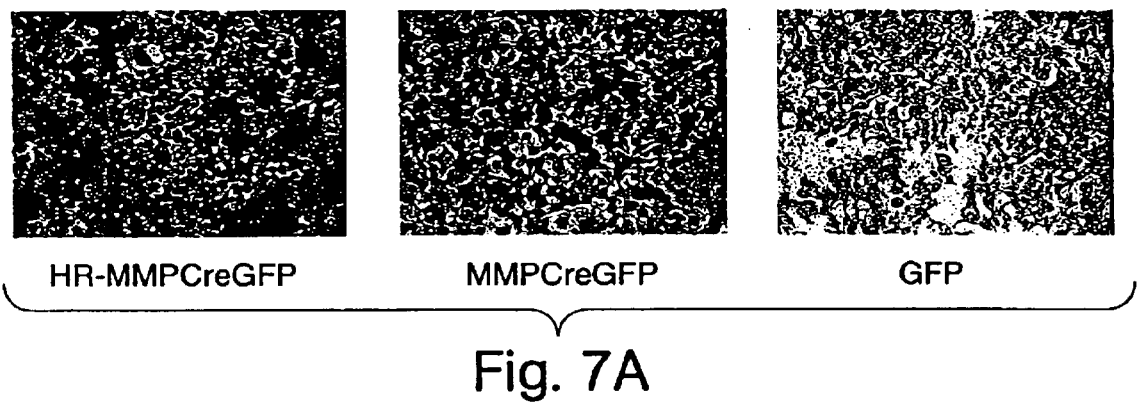
FIGS. 7A–D show that the HR-MMPcreGFP virus triggers efficient deletion of both a target bearing flanking lox sites and of its own coding sequence without causing measurable toxicity.

Concentrated stocks of MMPcreGFP and HR-MMPcreGFP were used to infect 293×Lac cells. Similar numbers of 13-galactosidase-positive cells were observed 2 days after infection by the two viruses (FIG. 7A, darkly stained cells). In contrast, infection with a GFP-encoding virus produced no β-galactosidase positive cells (FIG. 7A), suggesting that HR-MMPcreGFP and its non hit and run relative are capable of causing equally efficient recombination between lox P sites in trans. Subsequent experiments using HR-MMPcreGFP to infect MEFs with lox sites flanking portions of BRCA1 or BRCA2 coding sequences (D. Silver, S. Ganesan, J. Jonkers, A. Berns, and D. Livingston), MEFs with lox sites near the K-ras locus (D. Tuveson, D. Silver, D. Livingston, and T. Jacks), or osteoblasts with lox sites flanking part of the coding sequence of Rb (D. Thomas, D. Silver, D. Livingston, P. Hinds) have shown that deletion of sequences between lox P sites can be achieved with >90% efficiency (unpublished data).

Figure 7B:
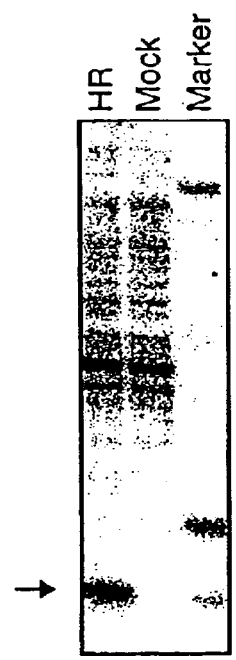

To investigate the details of cre-mediated self-excision of HR-MMPcreGFP, the structure of the provirus resulting from infection was examined. Southern blotting of genomic DNA from cells prepared six days after infection failed to detect a cre gene signal after cleavage with restriction enzymes that recognize sequences located within the proviral sequences that flank the cre gene (data not shown). A unique Stu I restriction site was added adjacent to the lox 511 site in the 3' LTR during construction of HR-MMPcreGFP (FIG. 6, asterisk), allowing this LTR to be readily distinguished from endogenous mouse retroviral LTRs. FIG. 7B shows a Southern blot of DNA from infected MEFs probed with a Moloney virus LTR. Despite the absence of a cre gene hybridization signal, six days after infection with HR-MMPcreGFP a restriction fragment of the expected size for the lox 511 containing LTR was detected (FIG. 7B, first lane, arrow). Thus, HR-MMPcreGFP appears to infect a cell, engineer the deletion of its own cre sequences, and leave an LTR behind, as depicted in FIG. 6. This type of Southern analysis also provides a means for determining the number of integrated proviral copies of HR-MMPcreGFP. The standard infection conditions employed here lead to an average of 1–4 proviruses per cell.

Figure 7C:
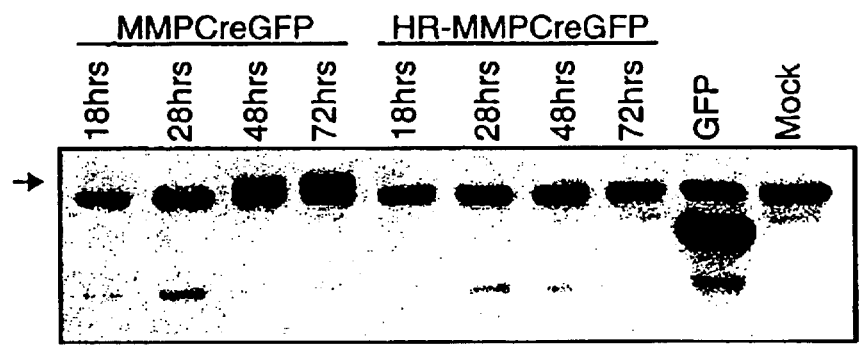

Further evidence concerning the mechanism of action of HR-MMPcreGFP is shown in FIG. 7C. Here, production of the cre recombinase protein was analyzed as a function of time after infection. 293×Lac cells were infected with equal amounts of concentrated supernatants of either MMPcreGFP or HR-MMPcreGFP virus. Infection with equivalent dilutions of these stocks led to the appearance of similar numbers of β-galactosidase positive cells (FIG. 7A), indicating a roughly equal ability of these stocks to promote recombination between lox sites. Lysates of these cells generated at different times after parallel infection with the two viruses were subjected to western blotting and probed with an anti-GFP antibody. Significant quantities of creGFP fusion protein were observed in cells infected with MMPcreGFP, beginning 48 hours after infection (FIG. 7C, arrow), but no appreciable creGFP fusion protein was detected in cells infected with HR-MMPcreGFP. Thus, the amount of creGFP fusion protein needed for self-excision and excision of a target elsewhere in the genome is below the limit of detection of this assay. Moreover, self-excision of HR-MMPcreGFP limits the duration and intensity of cre recombinase expression to a level significantly below that of a typical retroviral vector without compromising the ability to excise sequences between lox sites.

Example 3

Hit and Run Virus Does Not Cause Observable Toxicity

Figure 5B:
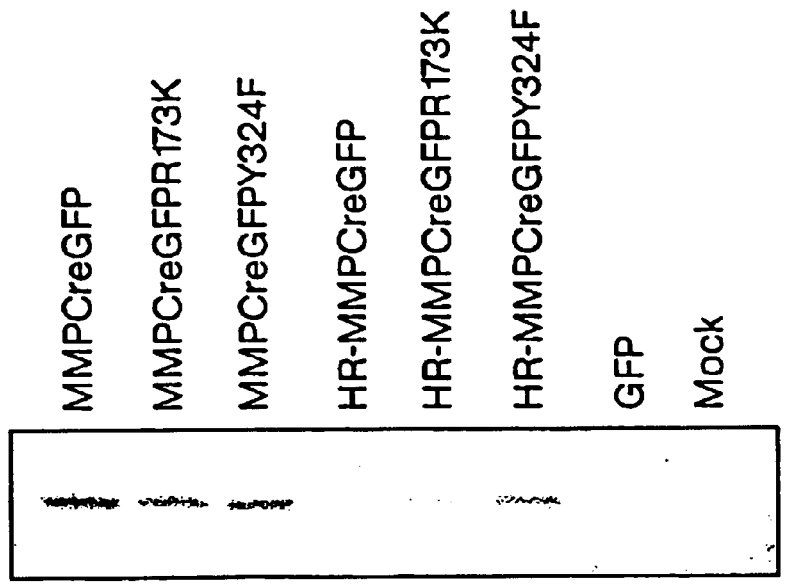
Figure 7D:
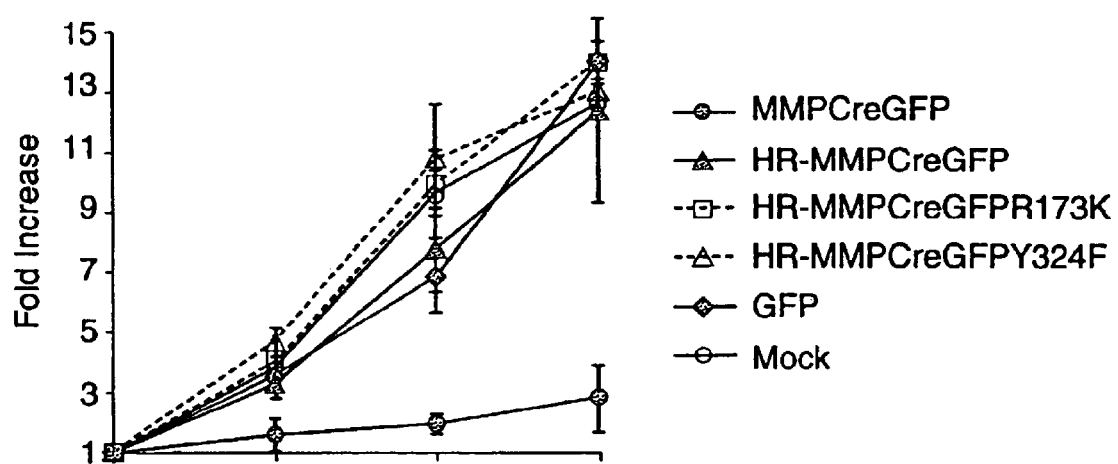

We have observed no phenotypic changes like those shown in FIG. 1A in a variety of cell lines infected with HR-MMPcreGFP, despite prolonged culture and efficient excision of a "floxed" target sequence (data not shown). As a more specific test, MEFs were infected with HR-MMPcreGFP or identical viruses that bear the mutant cre alleles described above that bind to lox sites but do not cleave DNA. Cell proliferation analysis was performed identically and as part of the experiment reported in FIG. 5A; the results are shown in FIG. 7D. Mock-infected MEFs and MEFs infected with HR-MMPcreGFP, HR-MMPcreGFPR173K, HR-MMPcreGFPY324F, or a GFP-only encoding virus, proliferated at virtually identical rates. These results stand in contrast to what was observed with MEFs infected with MMPcreGFP, a virus identical to HR-MMPcreGFP but lacking lox 511 sites and, thus, unable to self-excise. To investigate expression levels of the creGFP alleles in this experiment, a western blot for cre was performed on extracts obtained from cells on day 2 of this growth curve experiment (FIG. 5B, lanes 4–6). The data reveal that HR-MMPcreGFPR173K and HR-MMPcreGFPY324F express mutant creGFP fusion proteins at levels similar to those in cells infected with identical viruses that lack LTR-embedded lox 511 sites (FIG. 5B, lanes 1–3), consistent with lack of self-excision of these mutant cre viruses even though they contain lox 511 sites. Once again, because of self-excision, no cre-GFP fusion protein was detected in cells infected with HR-MMPcreGFP (FIG. 5B, lane 4). Therefore, with respect to morphology and proliferative capacity, cells infected with self-excising wt creGFP virus were indistinguishable from mock-infected cells, in sharp contrast to cells infected with an identical virus that cannot self-excise.

To understand better the mechanism of cre-dependent toxicity, metaphase chromosomes were prepared from wt MEFs nine days after infection with MMPcreGFP, MMPcreGFPR173K, HR-MMPcreGFP, or mock-infection. Cells infected with MMPcreGFP demonstrated an increase in the percentage of metaphase spreads showing overt chromosomal abnormalities including gaps, breaks, and fragments, and a striking increase in the absolute number of such abnormalities per spread (Table 1; see FIG. 8 for a dramatically abnormal spread). Furthermore, a higher percentage of metaphases obtained from cells infected with MMPcreGFP revealed aneuploidy than was observed in mock-infected cells or cells infected with Hit and Run or the mutant cre-encoding viruses (Table 1 and FIG. 8). Taken together, these results strongly suggest that prolonged exposure to a cre protein capable of strand scission leads, directly or indirectly, to genetic instability and that these abnormalities can be avoided by use of the Hit and Run virus.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid molecule comprising at least a first signal sequence and a second signal sequence and a recombinase gene operably linked to an expression control sequence, said first and second signal sequences being positioned to mediate in inversion of a sufficient portion of either the recombinase gene or the expression control sequence to inactivate or decrease recombinase activity when the first and second signal sequences contacted with a recombinase, thereby decreasing or eliminating recombinase-mediated toxicity.

2. The nucleic acid molecule of claim 1, wherein said nucleic acid molecule is included in a retioviral vector and said signal sequence is inserted to a retroviral long terminal repeat of said vector.

3. The nucleic acid molecule of claim 2, wherein said signal sequence is inserted into the U3 region of the 3' retroviral long terminal repeat of said vector.

4. The nucleic acid molecule of claim 1, wherein said recombinase is selected from the group consisting of a cre recombinase and a Flp recombinase and the signal sequence is selected from the group consisting of lox sequences and FRT sequences.

5. The nucleic acid molecule of claim 1, wherein said signal sequences flank said recombinase gene or said expression control sequence of said recombinase gene.

6. An isolated cell comprising the nucleic acid molecule of claim 1.

7. The isolated cell of claim 6, further comprising a second nucleic acid molecule comprising a target gene and signal sequences recognized by said recombinase.

8. The isolated cell of claim 7, wherein said recombinase, when expressed in said cell, inverts a sequence in said second nucleic acid molecule that is located between said signal sequences in said second nucleic acid molecule, and the inversion results in modulation of expression of said target gene.

9. The isolated cell of claim 8, wherein said signal sequences in said second nucleic acid molecule are in inverted orientation with respect to one another.

10. The isolated cell of claim 9, wherein said signal sequences in said second nucleic acid molecule flank said target gene, so that expression of said recombinase results in inversion of said target gene, and inactivation of expression of said target gene.

11. The isolated cell of claim 9, wherein said signal sequences in said second nucleic acid molecule flank a positive regulatory element of said target gene, so that expression of said recombinase results in inversion of said positive regulatory element, and inactivation of expression of said target gene.

12. A isolated cell comprising two nucleic acid molecules, wherein the first nucleic acid molecule comprises a recombinase gene operably linked to an expression control sequence and signal sequences recognized by a recombinase and the second nucleic acid molecule comprises a target gene and signal sequences recognized by a recombinase, wherein said signal sequences in said second nucleic acid molecule flank a negative regulatory element of said target gene, so that expression of said recombinase results in excision of said negative regulatory element, and activation of expression of said target gene.

13. A isolated cell comprising two nucleic acid molecules, wherein the first nucleic acid molecule comprises a recombinase gene operably linked to an expression control sequence and signal sequences recognized by a recombinase and the second nucleic acid molecule comprises a target gene and signal sequences recognized by a recombinase, wherein said signal sequences in said second nucleic acid molecule are in an inverted orientation with respect to one another.

14. The isolated cell of claim 13, wherein said signal sequences in said second nucleic acid molecule flank an inverted positive regulatory element of said target gene or an inverted coding region of said target gene, so that expression of said recombinase results in inversion of said inverted positive regulatory element or inversion of said inverted coding region, and activation of expression of said target gene.

15. The isolated cell of claim 13, wherein said signal sequences in said second nucleic acid molecule flank an inverted negative regulatory element of said target gene or a coding region of said target gone, so that expression of said recombinase results in inversion of said inverted negative regulatory element or inversion of said coding region, inactivation of expression of said target gene.

16. The isolated cell of claim 6, wherein said signal sequences in said nucleic acid molecule comprising said sequence encoding said recombinase flank said nucleic acid sequence encoding said recombinase.

17. The isolated cell of claim 6, wherein said signal sequences in said nucleic acid molecule comprising said sequence encoding said recombinase flank a positive regulatory element of said nucleic acid sequence encoding recombinase.

18. The isolated cell of claim 7, wherein said nucleic acid molecule comprising said sequence encoding said recombinase and said second nucleic molecule are present in the same vector.

19. A isolated cell comprising two nucleic acid molecules, wherein the first nucleic acid molecule, comprising a recombinase gene operably linked to an expression control sequence and signal sequences recognized by a recombinase and the second nucleic acid molecule, comprising a target gene and signal sequences recognized by a recombinase, are present in separate vectors.

20. The nucleic acid molecule of claim 1, wherein said signal sequences are in inverted orientation with respect to one another.

* * * * *